US012603149B2

(12) United States Patent
Chen et al.

(10) Patent No.: US 12,603,149 B2
(45) Date of Patent: Apr. 14, 2026

(54) VALIDATION METHODS AND SYSTEMS FOR SEQUENCE VARIANT CALLS

(71) Applicant: ILLUMINA, INC., San Diego, CA (US)

(72) Inventors: Xiao Chen, La Jolla, CA (US); Chen Zhao, San Diego, CA (US); Jessica Gordon, San Diego, CA (US); Shile Zhang, San Diego, CA (US); Tingting Jiang, San Diego, CA (US); Gwenn Berry, San Diego, CA (US); Yesha Shah, San Diego, CA (US); Han-Yu Chuang, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 920 days.

(21) Appl. No.: 16/348,832

(22) PCT Filed: Nov. 14, 2017

(86) PCT No.: PCT/US2017/061554

§ 371 (c)(1),
(2) Date: May 9, 2019

(87) PCT Pub. No.: WO2018/093780

PCT Pub. Date: May 24, 2018

(65) Prior Publication Data

US 2019/0348149 A1 Nov. 14, 2019

Related U.S. Application Data

(60) Provisional application No. 62/447,076, filed on Jan. 17, 2017, provisional application No. 62/422,841, filed on Nov. 16, 2016.

(51) Int. Cl.
G16B 20/20 (2019.01)
G06F 17/18 (2006.01)
G16B 30/00 (2019.01)

(52) U.S. Cl.
CPC ............. G16B 20/20 (2019.02); G06F 17/18 (2013.01); G16B 30/00 (2019.02)

(58) Field of Classification Search
CPC .......... G06F 17/18; G16B 20/20; G16B 30/00
See application file for complete search history.

(56) References Cited

U.S. PATENT DOCUMENTS

| | | | |
|---|---|---|---|
| 5,641,658 | A | 6/1997 | Adams et al. |
| 6,260,034 | B1 | 7/2001 | Bjorkesten |
| 7,057,026 | B2 | 6/2006 | Barnes et al. |
| 7,115,400 | B1 | 10/2006 | Adessi et al. |
| 7,211,414 | B2 | 5/2007 | Hardin et al. |
| 7,315,019 | B2 | 1/2008 | Turner et al. |
| 7,329,492 | B2 | 2/2008 | Hardin et al. |
| 7,405,281 | B2 | 7/2008 | Xu et al. |
| 9,115,353 | B2 | 8/2015 | Klausing et al. |
| 2002/0055100 | A1 | 5/2002 | Kawashima et al. |
| 2004/0002090 | A1 | 1/2004 | Mayer et al. |
| 2004/0096853 | A1 | 5/2004 | Mayer |
| 2007/0099208 | A1 | 5/2007 | Drmanac et al. |
| 2007/0128624 | A1 | 6/2007 | Gormley et al. |
| 2007/0166705 | A1 | 7/2007 | Milton et al. |
| 2008/0009420 | A1 | 1/2008 | Schroth et al. |
| 2008/0108082 | A1 | 5/2008 | Rank et al. |
| 2008/0280773 | A1 | 11/2008 | Fedurco et al. |
| 2009/0088327 | A1 | 4/2009 | Rigatti et al. |
| 2012/0203792 | A1 | 8/2012 | Zheng et al. |
| 2013/0110407 | A1 | 5/2013 | Baccash et al. |
| 2013/0296175 | A1 | 11/2013 | Rafnar et al. |
| 2014/0280327 | A1 | 9/2014 | Pham et al. |
| 2014/0304270 | A1 | 10/2014 | Torkamani et al. |
| 2015/0324519 | A1 | 11/2015 | Liu |
| 2015/0337388 | A1 | 11/2015 | Garner et al. |
| 2016/0085910 | A1 | 3/2016 | Bruand et al. |
| 2016/0283655 | A1 | 9/2016 | Ye et al. |
| 2017/0286594 | A1 | 10/2017 | Reid et al. |
| 2018/0060482 | A1 | 3/2018 | Nadauld et al. |

FOREIGN PATENT DOCUMENTS

| | | | | |
|---|---|---|---|---|
| CA | 2894317 | A1 | 12/2016 | |
| EP | 2614161 | B1 * | 11/2020 | ............. G16B 20/00 |
| JP | 2012-235723 | | 12/2012 | |
| KR | 10-2015-0094820 | | 7/2014 | |
| KR | 10-2016-0047506 | | 5/2016 | |
| WO | WO 91/06678 | | 5/1991 | |
| WO | WO 04/018497 | | 3/2004 | |
| WO | WO 07/010252 | | 1/2007 | |
| WO | WO 07/123744 | | 11/2007 | |
| WO | WO 12/092426 | | 7/2012 | |
| WO | 2013070634 | A1 | 5/2013 | |

(Continued)

OTHER PUBLICATIONS

Fay, M.P. and Proschan, M.A., 2010. Wilcoxon-Mann-Whitney or t-test? On assumptions for hypothesis tests and multiple interpretations of decision rules. Statistics surveys, 4, p. 1-39. (Year: 2010).*

(Continued)

*Primary Examiner* — Olivia M. Wise
*Assistant Examiner* — Janna Nicole Schultzhaus
(74) *Attorney, Agent, or Firm* — Knobbe, Martens, Olson & Bear, LLP

(57) ABSTRACT

Methods and systems are provided for validating variant calls. Sequencing data is received for a sample read along the genomic sequence of interest. An indication is received of a potential variant call at a designated position within the sequence of nucleotides along the genomic sequence of interest. The methods and systems obtain baseline variant frequencies at the designated position within one or more baseline genomic sequences, determine a sample variant frequency at the designated position for the genomic sequence of interest, analyze the baseline and sample variant frequencies at the designated position to obtain a quality score, and validate the potential variant call for the genomic sequence of interest based on the quality score.

12 Claims, 9 Drawing Sheets

(56)                    References Cited

FOREIGN PATENT DOCUMENTS

| | | |
|---|---|---|
| WO | WO 15/173222 | 11/2015 |
| WO | WO 16/061396 | 4/2016 |
| WO | WO 17/114810 | 7/2017 |
| WO | 2018006152 A1 | 1/2018 |
| WO | WO 18/064547 | 4/2018 |
| WO | WO 19/200338 | 10/2019 |

OTHER PUBLICATIONS

Evans, M.F. The polymerase chain reaction and pathology practice. Diagnostic Histopathology, 15(7), pp. 344-356. (Year: 2009).*

Albers, C. , et al., "Dindel: Accurate indel calls from short-read data", Genome Research vol. 21(6), Jun. 1, 2011, 961-973.

Angermueller, C. , et al., "Deep learning for computational biology", Molecular Systems Biology, 2016, 16 pages.

Depristo, M. , et al., "A framework for variation discovery and genotyping using next-generation DNA sequencing data", Nature Genetics vol. 43 (5), Apr. 10, 2011, p. 1-20.

Krawitz, P. , et al., "Microindel detection in short-read sequence data", Bioinformatics vol. 26(6) doi:10.1093/bioinformatics/btq027, 2010, 722-729.

Nothaft, F. , "Scalable Genome Resequencing with ADAM and avocado", Mar. 12, 2015, 22-25.

Rimmer, A. , et al., "Integrating mapping-, assembly- and haplotype-based approaches for calling variants in clinical sequencing applicaitons", Nature Genetics vol. 46(8), Aug. 2014, 912-918.

Rimmer, A. , et al., "Supplementary Information for Intergrating mapping, assembly and haplotype-based approaches for calling variants in clinical sequencing applicaitons", Nature Genetics vol. 48(1), Aug. 1, 2014, 912-918.

Saunders, C. , et al., "Strelka: accurate somatic small-variant calling from sequenced tumor-normal sample pairs", Bioinformatics vol. 28(14), 2012, 1811-1817.

Torracinta, R/ , et al., "Adaptive Somatic Mutations Calls with Deep Learning and Semi-Simulated Data", bioRxiv doi: http://dx.doi.org/10.1101/079087. The, Oct. 4, 2016, 1-13.

Ajawatanawong et al., Jun. 2012, SeqFIRE: a web application for automated extraction of indel regions and conserved blocks from protein multiple sequence alignments, Nucleic Acids Research, 40:340-347.

Bentley et al., Nov. 6, 2008, Accurate whole human genome sequencing using reversible terminator chemistry, Nature, 456:53-59 and supplementary information.

Budowle et al., Sep. 2010, Automated alignment and nomenclature for consistent treatment of polymorphisms in the human mitochondrial DNA control region, Journal of Forensic Science, 55(5):1190-1195.

Chen et al., 2016, Manta: rapid detection of structural variants and indels for germline and cancer sequencing applications, Bioinformatics, 32(8):1220-1222.

Dijke, Jun. 17, 2017, Convolutional Neural Networks for Regulatory Genomics, Universiteit Leiden Opleiding nformatica, Master's Thesis, Leiden Institute of Advanced Computer Science (LIACS), Leiden University, The Netherlands, 58 pp.

Dong et al., 2015, Comparison and integration of deleteriousness prediction methods for non-synonymous SNVs in whole exome sequencing studies, Human Molecular Genetics, 24(8):2125-2137.

Dunn et al., Aug. 20-23, 2017, Pisces: An Accurate and Versatile Single Sample Somatic and Germline Variant Caller, ACM-BCB'17, Boston, MA, Poster Session, 1 page.

Dunn et al., Mar. 20, 2018, Pisces: An Accurate and Versatile Variant Caller for Somatic and Germline Next-Generation Sequencing Data, Bioinfomrtics, 35(9):1579-1581.

Friedman, Dec. 2017, Deep-learning in GATK4, blog post, 11 pages.

Genome sequencing analysis of cancer by Illumina HiSeq2000 [online], RIKEN Research Institute Genome Medical Science Research Center, Aug. 21, 2012, https://jp.illumina.com/content/dam/illumina-marketing/apac/japan/documents/pdf/2012_illumina_hiseq2000-cancer.pdf, p. 1-59.

Goodfellow et al., 2016, Chapter 9: Convolutional Networks, in Deep Learning, MIT Press, pp. 326-366.

Hasan et al., 2015, Performance evaluation of indel calling tools using real short-read data, Human Genomics, 9:20, 14 pp.

Homer et al., 2010, Improved variant discovery through local re-alignment of short-read next-generation sequencing data using SRMA, Genome Biology, 11:R99, 12 pp.

Illumina, 2010, Complete Secondary Analysis Workflow for the Genome Analyzer, Technical Note: Systems and Software, 5 pp.

Illumina, 2011, Quality Scores for Next-Generation Sequencing, Technical Note: Sequencing, 2 pp.

Illumina, Apr. 23, 2014, Understanding Illumina Quality Scores, Technical Note: infomatics, 2 pp.

Illumina, Germline Empirical Variant Score (EVS) Model Training, User Guide, accessed Jul. 21, 2023 https://github.com/Illumina/strelka/blob/master/docs/userGuide/trainingGermlineEmpiricalScore.md, 6 pp.

Illumina, Pisces, Github, retrieved on Jul. 21, 2023, https://github.com/ Ilumina/Pisces, 4 pp.

Illumina, Strelka User Guide, GitHub, retrieved Jul. 21, 2023, https://github.com/Illumina/strelka/tree/master/docs/userGuide, 17 pp.

Illumina, Strelka2 germline and somatic small variant caller, GitHub, retrieved on Jul. 21, 2023, https://github.com/Illumina/strelka, 3 pp.

Kim et al., Sep. 2017, Strelka 2 Fast and accurate variant calling for clinical sequencing applications, bioRxiv doi: ttps://doi.org/10.1101/192872, with supplementary information, p. 1-32.

Kothen-Hill et al., Feb. 16, 2018, Deep learning mutation prediction enables early state lung cancer detection in liquid biopsy, ICLR 2018 Conference, 24 pp.

Li et al., 2008, Mapping short DNA sequencing reads and calling variants using mapping quality scores, Genome Research, 18(11):1851-1858.

Lizardi et al., Jul. 1998, Mutation detection and single-molecule counting using isothermal rolling-circle amplification, Nat. Genet. 19:225-232.

McKenna et al., 2010, The genome analysis toolkit: a map-reduce framework for analyzing next-generation DNA sequencing data, Genome Research 20:1297-1303.

Novelli et al., Sep. 2017, Current Challenges in Cardiovascular Molecular diagnostics, Frontiers in Cardiovascular Medicine, 4(54):1-3.

Patterson et al., Aug. 2017, Deep learning: a practitioner's approach, O'Reilly Media, Inc. (TOC), p. 1-19.

Poplin et al., Mar. 20, 2018, Creating a universal SNP and small indel variant caller with deep neural networks, bioRxiv preprpint, doi: https://doi.org/10.1101/092890, 24 pp.

Ramachandram et al., Nov. 13, 2017, Deep Multimodal Learning, IEEE Signal Processing Magazine, 34(6):96-108.

Ravasio et al., Jun. 14, 2017, GARFIELD-NGS: Genomic vARiants Flitering by dEep Learning moDels in NGS, bioRxiv preprint doi: https://doi.org/10.1101/149146, 18 pp.

Sifrim et al., 2012, Annotate-it: a Swiss-knife approach to annotation, analysis and interpretation of single nucleotide ariation in human disease, Genome Medicine, 4:73, 12 pp.

Spinella et al., 2016, SNooPer: a machine learning-based method for somatic variant identification from low-pass next- peneration sequencing, BMC Genomics, 17:912, 11 pp.

Strom, Jan. 6, 2016, Current practices and guidelines for clinical next-generation sequencing oncology testing, Cancer Biology & Medicine, 9 pp.

Stromberg et al, Aug. 20-23, 2017, Nirvana: Clinical Grade Variant Annotator, ACM-BCB 2017 Poster Session, Boston, MA, 1 p.

Takata et al., 2011, Exome sequencing identifies a novel missense variant in RRM2B associated with autosomal recessive progressive external ophthalmoplegia, Genome Biology, 12:R92, 7 pp.

Vijayan et al., 2018, Improving somatic variant identification through integration of genome and exome data, BMC Genomics, 18(Suppl 7):748, pp. 63-71.

Wu, May 1, 2017, Introduction to Convolutional Neural Networks, Nanjing University, 31 pp.

(56)     References Cited

OTHER PUBLICATIONS

Xu, 2018, A review of somatic single nucleotide variant calling algorithms for next-generation sequencing data, Comput Struct Biotechnol J., 16:15-24.
Yu et al., Sep. 2018, Survey on encoding schemes for genomic data representation and feature learning-from signal processing to machine learning, Big Data Mining and Analytics 1(3):191-210.

\* cited by examiner

VALIDATION METHODS AND SYSTEMS FOR SEQUENCE VARIANT CALLS

RELATED APPLICATION

The present application relates, and claims the benefit of priority, to U.S. Provisional Patent Application No. 62/447,076, titled "Validation Methods and Systems for Sequence Variant Calls", filed Jan. 17, 2017 and U.S. Provisional Patent Application No. 62/422,841, titled "Methods and Systems to Improve Accuracy in Variant Calling", filed Nov. 16, 2016, the complete subject matter of which is incorporated by reference in their entirety.

BACKGROUND

The subject matter herein relates generally to systems and methods for analyzing sequencing operations and more particularly to validating variant calls made in connection with sequencing operations.

Today cancer treatment techniques are shifting away from a one-drug-fits-all approach. Comprehensive diagnostic approaches raise challenges for methods that detect DNA variants. Non-limiting examples of DNA detection methods include Sanger sequencing, immunohistochemistry (IHC), fluorescence in situ hybridization (FISH), and quantitative PCR (qPCR). Some detection methods analyze the DNA for one or few genetic changes at a time. However, as the number of DNA alterations known to drive cancer progression continues to grow, new methods are proposed to analyze DNA for more and more genetic changes during one sequencing operation.

Next-generation sequencing (NGS) offers an ability to assess variants in multiple genes using one sample. To that end, a system has been proposed that offers a hybrid capture based NGS test (assay) that targets multiple cancer genes (e.g., over 100 cancer genes) for sequencing on the Next-Seq™ and HiSeq™ platforms. The NGS test includes a DNA workflow for the identification of single nucleotide variants (SNVs), small insertions and deletions (indels), multiple nucleotide variants (MNVs), gene amplifications (CNVs). The NGS test also includes a RNA workflow for the identification of splice variants and gene fusions. A variant is identified when a sample nucleic acid sequence is determined to different from a reference sequence at one or more base pair positions along the sequence. Both DNA and RNA alterations from different genes can be assessed at a common point in time while sequencing a single sample.

Bioinformatics analysis techniques are being developed that deliver variant calls in a rapid turnaround time. The techniques include, among other things, an aligner and variant caller. The alignment process is able to align long indels to overcome the challenges from shotgun sequencing with short read length. Further, NGS tests utilize various sample preparation techniques, one example of which is formalin-fixed, paraffin-embedded (FFPE). FFPE samples present another difficulty for detecting DNA variants when the DNA of interest is of low abundance and/or may have degraded.

However, current proposed sequencing techniques experience false positives in connection with variant calling. For example, the technique may incorrectly determine that a variant is present in a sample sequence at a particular location (base pair) and/or incorrectly identify the type of variant (generally referred to as false positives). Systematic errors may cause false positives, such as due to FFPE artifacts, sequencing errors or PCR errors.

A need remains for sequencing methods and systems that can simultaneously interrogate multiple types of DNA variants, without declaring an unduly large number of false positives, in a single sample in a simple and cost-effective manner.

DEFINITIONS

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

As used herein, the following terms have the meanings indicated.

The term "chromosome" refers to the heredity-bearing gene carrier of a living cell, which is derived from chromatin strands comprising DNA and protein components (especially histones). The conventional internationally recognized individual human genome chromosome numbering system is employed herein.

The term "site" refers to a unique position (e.g., chromosome ID, chromosome position and orientation) on a reference genome. In some embodiments, a site may be a residue, a sequence tag, or a segment's position on a sequence. The term "locus" may be used to refer to the specific location of a nucleic acid sequence or polymorphism on a reference chromosome.

The term "sample" herein refers to a sample, typically derived from a biological fluid, cell, tissue, organ, or organism containing a nucleic acid or a mixture of nucleic acids containing at least one nucleic acid sequence that is to be sequenced and/or phased. Such samples include, but are not limited to sputum/oral fluid, amniotic fluid, blood, a blood fraction, fine needle biopsy samples (e.g., surgical biopsy, fine needle biopsy, etc.), urine, peritoneal fluid, pleural fluid, tissue explant, organ culture and any other tissue or cell preparation, or fraction or derivative thereof or isolated therefrom. Although the sample is often taken from a human subject (e.g., patient), samples can be taken from any organism having chromosomes, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc.

The term "sequence" includes or represents a strand of nucleotides coupled to each other. The nucleotides may be based on DNA or RNA. It should be understood that one sequence may include multiple sub-sequences. For example, a single sequence (e.g., of a PCR amplicon) may have 350 nucleotides. The sample read may include multiple sub-sequences within these 350 nucleotides. For instance, the sample read may include first and second flanking sub-sequences having, for example, 20-50 nucleotides. The first and second flanking sub-sequences may be located on either side of a repetitive segment having a corresponding sub-sequence (e.g., 40-100 nucleotides). Each of the flanking sub-sequences may include (or include portions of) a primer sub-sequence (e.g., 10-30 nucleotides). For ease of reading, the term "sub-sequence" will be referred to as "sequence," but it is understood that two sequences are not necessarily separate from each other on a common strand. To differentiate the various sequences described herein, the sequences may be given different labels (e.g., target sequence, primer sequence, flanking sequence, reference sequence, and the like). Other terms, such as "allele," may be given different labels to differentiate between like objects.

The term "paired-end sequencing" refers to sequencing methods that sequence both ends of a target fragment. Paired-end sequencing may facilitate detection of genomic rearrangements and repetitive segments, as well as gene fusions and novel transcripts. Methodology for paired-end sequencing are described in PCT publication WO07010252, PCT application Serial No. PCTGB2007/003798 and US patent application publication US 2009/0088327, each of which is incorporated by reference herein. The use of a tag sequence, for example as described in application WO05068656, whose contents are incorporated herein by reference in their entirety, allows multiple different samples to be analysed in the same sequencing whilst preserving the identity of each sample. In one example, a series of operations may be performed as follows; (a) generate clusters of nucleic acids; (b) linearize the nucleic acids; (c) hybridize a first sequencing primer and carry out repeated cycles of extension, scanning and deblocking, as set forth above; (d) "invert" the target nucleic acids on the flow cell surface by synthesizing a complimentary copy; (e) linearize the resynthesized strand; and (f) hybridize a second sequencing primer and carry out repeated cycles of extension, scanning and deblocking, as set forth above. The inversion operation can be carried out be delivering reagents as set forth above for a single cycle of bridge amplification.

The term "reference genome" or "reference sequence" refers to any particular known genome sequence, whether partial or complete, of any organism which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences. A genome includes both the genes and the non-coding sequences of the DNA. The reference sequence may be larger than the reads that are aligned to it. For example, it may be at least about 100 times larger, or at least about 1000 times larger, or at least about 10,000 times larger, or at least about 105 times larger, or at least about 106 times larger, or at least about $10^7$ times larger. In one example, the reference genome sequence is that of a full length human genome. In another example, the reference genome sequence is limited to a specific human chromosome such as chromosome 13. In some embodiments, a reference chromosome is a chromosome sequence from human genome version hg19. Such sequences may be referred to as chromosome reference sequences, although the term reference genome is intended to cover such sequences. Other examples of reference sequences include genomes of other species, as well as chromosomes, sub-chromosomal regions (such as strands), etc., of any species. In various embodiments, the reference genome is a consensus sequence or other combination derived from multiple individuals. However, in certain applications, the reference sequence may be taken from a particular individual.

The term "read" refer to a collection of sequence data that describes a fragment of a nucleotide sample or reference.

The term "read" may refer to a sample read and/or a reference read. Typically, though not necessarily, a read represents a short sequence of contiguous base pairs in the sample or reference. The read may be represented symbolically by the base pair sequence (in ATCG) of the sample or reference fragment. It may be stored in a memory device and processed as appropriate to determine whether the read matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

Next-generation sequencing methods include, for example, sequencing by synthesis technology (Illumina), pyrosequencing (454), ion semiconductor technology (Ion Torrent sequencing), single-molecule real-time sequencing (Pacific Biosciences) and sequencing by ligation (SOLiD sequencing). Depending on the sequencing methods, the length of each read may vary from about 30 bp to more than 10,000 bp. For example, Illumina sequencing method using SOLiD sequencer generates nucleic acid reads of about 50 bp. For another example, Ion Torrent Sequencing generates nucleic acid reads of up to 400 bp and 454 pyrosequencing generates nucleic acid reads of about 700 bp. For yet another example, single-molecule real-time sequencing methods may generate reads of 10,000 bp to 15,000 bp. Therefore, in certain embodiments, the nucleic acid sequence reads have a length of 30-100 bp, 50-200 bp, or 50-400 bp.

The terms "sample read", "sample sequence" or "sample fragment" refer to sequence data for a genomic sequence of interest from a sample. For example, the sample read comprises sequence data from a PCR amplicon having a forward and reverse primer sequence. The sequence data can be obtained from any select sequence methodology. The sample read can be, for example, from a sequencing-by-synthesis (SBS) reaction, a sequencing-by-ligation reaction, or any other suitable sequencing methodology for which it is desired to determine the length and/or identity of a repetitive element. The sample read can be a consensus (e.g., averaged or weighted) sequence derived from multiple sample reads. In certain embodiments, providing a reference sequence comprises identifying a locus-of-interest based upon the primer sequence of the PCR amplicon.

The term "raw fragment" refers to sequence data for a portion of a genomic sequence of interest that at least partially overlaps a designated position or secondary position of interest within a sample read or sample fragment. Non-limiting examples of raw fragments include a duplex stitched fragment, a simplex stitched fragment, a duplex un-stitched fragment and a simplex un-stitched fragment. The term "raw" is used to indicate that the raw fragment includes sequence data having some relation to the sequence data in a sample read, regardless of whether the raw fragment exhibits a supporting variant that corresponds to and authenticates or confirms a potential variant in a sample read. The term "raw fragment" does not indicate that the fragment necessarily includes a supporting variant that validates a variant call in a sample read. For example, when a sample read is determined by a variant call application to exhibit a first variant, the variant call application may determine that one or more raw fragments lack a corresponding type of "supporting" variant that may otherwise be expected to occur given the variant in the sample read.

The terms "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

The term "indel" refers to the insertion and/or the deletion of bases in the DNA of an organism. A micro-indel represents an indel that results in a net change of 1 to 50 nucleotides. In coding regions of the genome, unless the length of an indel is a multiple of 3, it will produce a frameshift mutation. Indels can be contrasted with point mutations. An indel inserts and deletes nucleotides from a sequence, while a point mutation is a form of substitution that replaces one of the nucleotides without changing the overall number in the DNA. Indels can also be contrasted with a Tandem Base Mutation (TBM), which may be defined as substitution at adjacent nucleotides (primarily substitutions at two adjacent nucleotides, but substitutions at three adjacent nucleotides have been observed.

The term "variant" refers to a nucleic acid sequence that is different from a nucleic acid reference. Typical nucleic acid sequence variant includes without limitation single nucleotide polymorphism (SNP), short deletion and insertion polymorphisms (Indel), copy number variation (CNV), microsatellite markers or short tandem repeats and structural variation. Somatic variant calling is the effort to identify variants present at low frequency in the DNA sample. Somatic variant calling is of interest in the context of cancer treatment. Cancer is caused by an accumulation of mutations in DNA. A DNA sample from a tumor is generally heterogeneous, including some normal cells, some cells at an early stage of cancer progression (with fewer mutations), and some late-stage cells (with more mutations). Because of this heterogeneity, when sequencing a tumor (e.g., from an FFPE sample), somatic mutations will often appear at a low frequency. For example, a SNV might be seen in only 10% of the reads covering a given base.

The term "variant frequency" represents the relative frequency of an allele (variant of a gene) at a particular locus in a population, expressed as a fraction or percentage. For example, the fraction or percentage may be the fraction of all chromosomes in the population that carry that allele. By way of example, sample variant frequency represents the relative frequency of an allele/variant at a particular locus/position along a genomic sequence of interest over a "population" corresponding to the number of reads and/or samples obtained for the genomic sequence of interest from an individual. As another example, a baseline variant frequency represents the relative frequency of an allele/variant at a particular locus/position along one or more baseline genomic sequences where the "population" corresponding to the number of reads and/or samples obtained for the one or more baseline genomic sequences from a population of normal individuals.

The terms "position", "designated position", and "locus" refer to a location or coordinate of one or more nucleotides within a sequence of nucleotides. The terms "position", "designated position", and "locus" also refer to a location or coordinate of one or more base pairs in a sequence of nucleotides.

The term "haplotype" refers to a combination of alleles at adjacent sites on a chromosome that are inherited together. A haplotype may be one locus, several loci, or an entire chromosome depending on the number of recombination events that have occurred between a given set of loci, if any occurred.

The term "threshold" herein refers to a numeric or non-numeric value that is used as a cutoff to characterize a sample, a nucleic acid, or portion thereof (e.g., a read). A threshold may be varied based upon empirical analysis. The threshold may be compared to a measured or calculated value to determine whether the source giving rise to such value suggests should be classified in a particular manner. Threshold values can be identified empirically or analytically. The choice of a threshold is dependent on the level of confidence that the user wishes to have to make the classification. The threshold may be chosen for a particular purpose (e.g., to balance sensitivity and selectivity). As used herein, the term "threshold" indicates a point at which a course of analysis may be changed and/or a point at which an action may be triggered. A threshold is not required to be a predetermined number. Instead, the threshold may be, for instance, a function that is based on a plurality of factors. The threshold may be adaptive to the circumstances. Moreover, a threshold may indicate an upper limit, a lower limit, or a range between limits.

In some embodiments, a metric or score that is based on sequencing data may be compared to the threshold. As used herein, the terms "metric" or "score" may include values or results that were determined from the sequencing data or may include functions that are based on the values or results that were determined from the sequencing data. Like a threshold, the metric or score may be adaptive to the circumstances. For instance, the metric or score may be a normalized value. As an example of a score or metric, one or more embodiments may use count scores when analyzing the data. A count score may be based on number of sample reads. The sample reads may have undergone one or more filtering stages such that the sample reads have at least one common characteristic or quality. For example, each of the sample reads that are used to determine a count score may have been aligned with a reference sequence or may be assigned as a potential allele. The number of sample reads having a common characteristic may be counted to determine a read count. Count scores may be based on the read count. In some embodiments, the count score may be a value that is equal to the read count. In other embodiments, the count score may be based on the read count and other information. For example, a count score may be based on the read count for a particular allele of a genetic locus and a total number of reads for the genetic locus. In some embodiments, the count score may be based on the read count and previously-obtained data for the genetic locus. In some embodiments, the count scores may be normalized scores between predetermined values. The count score may also be a function of read counts from other loci of a sample or a function of read counts from other samples that were concurrently run with the sample-of-interest. For instance, the count score may be a function of the read count of a particular allele and the read counts of other loci in the sample and/or the read counts from other samples. As one example, the read counts from other loci and/or the read counts from other samples may be used to normalize the count score for the particular allele.

The terms "coverage" or "fragment coverage" refer to a count or other measure of a number of sample reads for the same fragment of a sequence. A read count may represent a count of the number of reads that cover a corresponding fragment. Alternatively, the coverage may be determined by multiplying the read count by a designated factor that is based on historical knowledge, knowledge of the sample, knowledge of the locus, etc.

SUMMARY

In accordance with embodiments herein, a computer implemented method is provided for validating variant calls. The method operates under control of one or more processors executing program instructions for, receiving sequencing data including a sample read that has a corresponding sequence of nucleotides along the genomic sequence of interest, receiving an indication of a potential variant call at a designated position within the sequence of nucleotides along the genomic sequence of interest, and obtaining baseline variant frequencies at the designated position within one or more baseline genomic sequences. The method obtains a sample variant frequency at the designated position for the genomic sequence of interest. The method analyzes the baseline and sample variant frequencies at the designated position to obtain a quality score; and validates the potential variant call for the genomic sequence of interest based on the quality score.

Optionally, the analyzing operation includes obtaining a relation between the sample variant frequency and a distribution of the baseline variant frequencies, the quality score based on the relation. Optionally, the analyzing operation comprises indexing the sample variant frequency with respect to a distribution of the baseline variant frequencies. The relation may be based on a non-parametric Wilcoxon rank sum test. The baseline variant frequencies indicate a degree of background noise at corresponding positions along the baseline genomic sequence.

Optionally, the validating further comprises comparing the quality score to a threshold; and declaring the potential variant call to be a valid variant call when the quality score exceeds the threshold. The baseline variant frequencies may be derived from multiple baseline genomic sequences that are associated with more than one type of allele. Optionally, the method further comprises receiving sequencing data that includes a plurality of reference reads of a sequence of nucleotides along the baseline genomic sequence, and determining the baseline variant frequencies for the reference reads at the designated positions. The determining of the baseline variant frequencies may further comprise receiving the sequencing data from the reference reads for a set of positions within a current base pair window; identifying a candidate variant frequency for one or more positions in the set of positions within the current base pair window; selecting one of the candidate variant frequencies as the baseline variant frequency for a designated position within the reference read; and shifting the base pair window along the baseline genomic sequence and repeating the operations In accordance with an embodiment, a computer implemented method is provided for validating variant calls. The method operations under control of one or more processors executing program instructions for, receiving an indication of a potential variant call for a genomic sequence of interest; and receiving sequencing data including reads for sample and raw fragments of nucleotides along the genomic sequence of interest, the reads including sample reads for the sample fragment corresponding to a sequence of nucleotides at designated position along the genomic sequence of interest. The method analyzes a sample variant frequency at the designated position for the genomic sequence of interest with respect to baseline variant frequencies at the designated position for a baseline genomic sequence to obtain a quality score; and determining at least one of the following: A) whether the raw fragments confirm the potential variant call; B) whether the sample reads provide a predetermined amount of coverage for the sample fragment; and C) whether the potential variant call matches a prior variant call exhibited across a predefined population. The method validates the potential variant call based on the quality score and the determining operation.

Optionally, the determining may include operation A) and operation A) comprises: identifying the raw fragments that indicate a supporting variant call; obtaining a weighted fragment score for the raw fragments that indicate the supporting variant call; and comparing the weighted fragment score to a raw fragment threshold to determine whether to confirm the potential variant call.

Optionally, the determining may include operation A), wherein the raw fragments correspond to at least one of a duplex stitched fragment, a simplex stitched fragment, a duplex un-stitched fragment or a simplex un-stitched fragment. Optionally, the determining may include operation A) and operation A) may comprise: identifying a duplex stitched fragment as the raw fragment; and determining whether the duplex stitched fragment indicate a supporting variant call to determine whether to confirm the potential variant call. Optionally, the determining operation may include operation B), wherein the potential variant call is declared a No-call when the sample reads fall below the predetermined amount of coverage. Optionally, the determining operation may include operation C). When a match is determined between the potential and prior variant calls, the determining operation performs at least one of operation A) or operation B) utilizing a first threshold. When a match does not exist between the potential and prior variant calls, the determining operation performing at least one of operation A) or operation B) utilizing a second threshold.

Optionally, the method may perform the analyzing operation and determining operations A), B) and C) in a hierarchy.

In accordance with embodiments herein, a system is provided for validating variant calls. The system comprises memory storing program instructions and sequencing data including a sample read that has a corresponding sequence of nucleotides along the genomic sequence of interest and one or more processors that execute the program instructions. The processors receive an indication of a potential variant call at a designated position within the sequence of nucleotides along the genomic sequence of interest; and obtain baseline variant frequencies at the designated position within one or more baseline genomic sequences. The processors determine a sample variant frequency at the designated position for the genomic sequence of interest; and analyze the baseline and sample variant frequencies at the designated position to obtain a quality score. The processors validate the potential variant call for the genomic sequence of interest based on the quality score.

Optionally, the processors may obtain a relation between the sample variant frequency and a distribution of the baseline variant frequencies, the quality score based on the relation. Optionally, the processors index the sample variant frequency with respect to a distribution of the baseline variant frequencies. Optionally, the baseline variant frequencies indicate a degree of background noise at a corresponding locus along the baseline genomic sequence. Optionally, the processors compare the quality score to a threshold; and outputs an indication that declares the potential variant call to be invalid based on the comparison. Optionally, the system further comprises memory that stores sequencing data that includes a plurality of reference reads of nucleotides along the baseline genomic sequence, the one or more processors to determine the baseline variant frequencies for the reference reads at the designated position.

In accordance with embodiments herein, a system is provided for validating variant calls. The system comprises memory storing program instructions and sequencing data including reads for sample and raw fragments of nucleotides along the genomic sequence of interest, the reads including sample reads for the sample fragment corresponding to a sequence of nucleotides at designated position along the genomic sequence of interest; and one or more processors that execute the program instructions. The processors receive an indication of a potential variant call for a genomic sequence of interest; and analyze a sample variant frequency at the designated position for the genomic sequence of interest with respect to baseline variant frequencies at the designated position for a baseline genomic sequence to obtain a quality score. The processors determine at least one of the following: A) whether the raw fragments confirm the potential variant call; B) whether the sample reads provide a predetermined amount of coverage for the sample fragment; and C) whether the potential variant call matches a prior variant call exhibited across a predefined population. The processors validate the potential variant call based on the quality score and the determining operation.

Optionally, the processors may determine whether the raw fragments confirm the potential variant call by identifying the raw fragments that indicate a supporting variant call; obtaining a weighted fragment score for the raw fragments that indicate the supporting variant call; and comparing the weighted fragment score to a raw fragment threshold to determine whether to confirm the potential variant call. The raw fragments may correspond to at least one of a duplex stitched fragment, a simplex stitched fragment, a duplex un-stitched fragment or a simplex un-stitched fragment.

In accordance with embodiments herein, systems and methods are described to reduce false positive variant calling from systematic errors. Systematic errors may arise due to various factors such as FFPE artifacts, sequencing errors, library preparation errors, PCR errors and the like. Variant calls are statically subjected to a locus specific background error distribution that may be compiled from a panel of FFPE normal samples with varied DNA quality from various tissues sequenced by the NGS-based assay. The same sequencing data of the FFPE normal samples may also be utilized to normalize systematic bias in read coverage caused by PCR, DNA quality, probe pull-down efficiency, or sequence GC content to reveal the true copy number alterations in a test sample. To further enlarge the signal to noise ratio in CNV calling, additional enhancer probes may be added in the hybrid capture to provide robust estimation of gene amplification. In accordance with embodiments herein, methods and systems are described that address noise problems and prevent systematic errors from contributing to false positive variant calls. In connection there with, a set of normal samples is used to identify systematic bias in order for the system to increase the calling stringency in tumor samples in regions with high background noise. For FFPE samples, normal FFPE samples may be used to construct the baseline. For ctDNA samples, normal genomic DNA data may be used to construct the baseline. The problems of conventional approaches that are described herein become particularly problematic in samples that exhibit low frequency variance, such as when trying to do variant calling of a tumor sample.

In accordance with embodiments herein, a method and system are provided for somatic variant post processing which addresses a problem of reducing false positive somatic variant calls. The method and system construct a variant frequency baseline from normal samples to adjust variant calling confidence in genomic regions with different background noise levels. Separating signal from noise is a challenge both for detecting somatic variants in noisy FFPE data and for ultra-low frequency tumor variant discovery in cell-free DNA data. Systematic false positives are commonly found in small variant calling. Systematic false positives may be introduced during experimental steps including library preparation and sequencing. In addition, there are regions in the human genome that are sensitive to alignment errors, such as repetitive regions or regions with low sequence complexity.

BRIEF DESCRIPTIONS OF THE DRAWINGS

The present application describes various methods and systems for carrying out the methods. At least some of the methods are illustrated in the Figures as a plurality of operations. However, it should be understood that embodiments are not limited to the operations illustrated in the Figures. Operations may be omitted, operations may be modified, and/or other operations may be added. Moreover, operations described herein may be combined, operations may be performed simultaneously, operations may be performed concurrently, operations may be split into multiple sub-operations, operations may be performed in a different order, or operations (or a series of operations) may be re-performed in an iterative fashion. In addition, although different methods are set forth herein, it should be understood that the different methods (or operations of the different methods) may be combined in other embodiments.

DETAILED DESCRIPTION

Figure 1A:
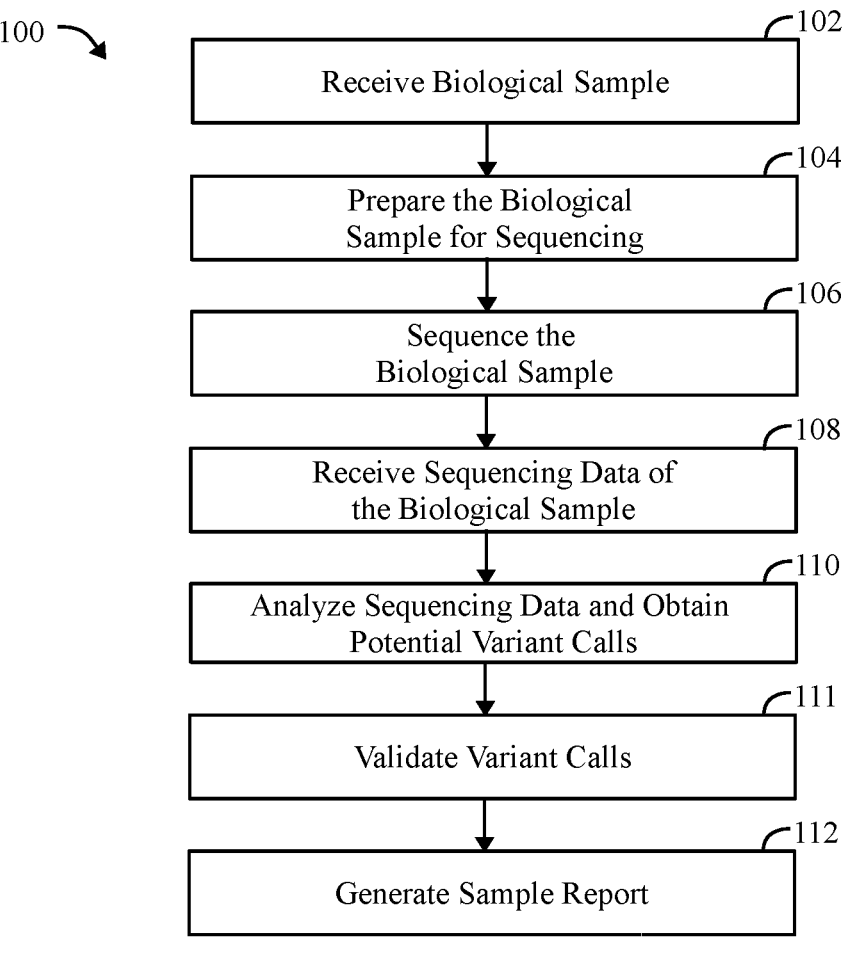
FIG. 1A illustrates a method for analyzing samples in accordance with an embodiment herein.

The detailed description of various embodiments will be better understood when read in conjunction with the appended drawings. To the extent that the Figures illustrate diagrams of the functional blocks of the various embodiments, the functional blocks are not necessarily indicative of the division between hardware circuitry. Thus, for example, one or more of the functional blocks (e.g., modules, processors, or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

Embodiments set forth herein may be applicable to analyzing nucleic acid sequences to identify sequence variations. Embodiments may be used to analyze potential variants/alleles of a genetic position/locus and determine a genotype of the genetic locus or, in other words, provide a genotype call for the locus. By way of example, nucleic acid sequences may be analyzed in accordance with the methods and systems described in US patent application publication 2016/0085910 and US patent application publication 2013/0296175, the complete subject matter of which are expressly Incorporated by reference herein in their entirety.

The method described herein may be implemented by one or more processors of various systems and devices executing program instructions stored in memory as described herein. Unless otherwise specified, the order of operations in the methods herein may be varied. In addition, one or more of the operations in the methods described herein may be omitted entirely, supplemented with additional operations.

Sequencing Process

FIG. 1A illustrates a method 100 in accordance with one embodiment. The method 100 includes receiving, at 102, a sample that includes or is suspected of including nucleic acids, such as DNA. The sample may be from a known or unknown source, such as an animal (e.g., human), plant, bacteria, or fungus. The sample may be taken directly from the source. For instance, blood or saliva may be taken directly from an individual. Alternatively, the sample may not be obtained directly from the source. At 104, one or more processors direct the system to prepare the sample for sequencing. The preparation 104 may include removing extraneous material and/or isolating certain material (e.g., DNA). The biological sample may be prepared to include features for a particular assay. For example, the biological sample may be prepared for sequencing-by-synthesis (SBS). In certain embodiments, the preparing may include amplification of certain regions of a genome. For instance, the preparing, at 104, may include amplifying predetermined genetic loci that are known to include STRs and/or SNPs. The genetic loci may be amplified using predetermined primer sequences.

At 106, the one or more processors direct the system to sequence the sample. The sequencing may be performed through a variety of known sequencing protocols. In particular embodiments, the sequencing includes SBS. In SBS, a plurality of fluorescently-labeled nucleotides are used to sequence a plurality of clusters of amplified DNA (possibly millions of clusters) present on the surface of an optical substrate (e.g., a surface that at least partially defines a channel in a flow cell). The flow cells may contain nucleic acid samples for sequencing where the flow cells are placed within the appropriate flow cell holders.

The nucleic acids can be prepared such that they comprise a known primer sequence that is adjacent to an unknown target sequence. To initiate the first SBS sequencing cycle, one or more differently labeled nucleotides, and DNA polymerase, etc., can be flowed into/through the flow cell by a fluid flow subsystem (not shown). Either a single type of nucleotide can be added at a time, or the nucleotides used in the sequencing procedure can be specially designed to possess a reversible termination property, thus allowing each cycle of the sequencing reaction to occur simultaneously in the presence of several types of labeled nucleotides (e.g., A, C, T, G). The nucleotides can include detectable label moieties such as fluorophores. Where the four nucleotides are mixed together, the polymerase is able to select the correct base to incorporate and each sequence is extended by a single base. Non-incorporated nucleotides can be washed away by flowing a wash solution through the flow cell. One or more lasers may excite the nucleic acids and induce fluorescence. The fluorescence emitted from the nucleic acids is based upon the fluorophores of the incorporated base, and different fluorophores may emit different wavelengths of emission light. A deblocking reagent can be added to the flow cell to remove reversible terminator groups from the DNA strands that were extended and detected. The deblocking reagent can then be washed away by flowing a wash solution through the flow cell. The flow cell is then ready for a further cycle of sequencing starting with introduction of a labeled nucleotide as set forth above. The fluidic and detection operations can be repeated several times to complete a sequencing run. Exemplary sequencing methods are described, for example, in Bentley et al., Nature 456: 53-59 (2008), International Publication No. WO 04/018497; U.S. Pat. No. 7,057,026; International Publication No. WO 91/06678; International Publication No. WO 07/123744; U.S. Pat. Nos. 7,329,492; 7,211,414; 7,315,019; 7,405,281, and U.S. Publication No. 2008/0108082, each of which is incorporated herein by reference.

In some embodiments, nucleic acids can be attached to a surface and amplified prior to or during sequencing. For example, amplification can be carried out using bridge amplification to form nucleic acid clusters on a surface. Useful bridge amplification methods are described, for example, in U.S. Pat. No. 5,641,658; U.S. Patent Publ. No. 2002/0055100; U.S. Pat. No. 7,115,400; U.S. Patent Publ. No. 2004/0096853; U.S. Patent Publ. No. 2004/0002090; U.S. Patent Publ. No. 2007/0128624; and U.S. Patent Publ. No. 2008/0009420, each of which is incorporated herein by reference in its entirety. Another useful method for amplifying nucleic acids on a surface is rolling circle amplification (RCA), for example, as described in Lizardi et al., Nat.

Genet. 19:225-232 (1998) and U.S. Patent Publ. No. 2007/ 0099208 A1, each of which is incorporated herein by reference.

One example SBS protocol exploits modified nucleotides having removable 3' blocks, for example, as described in International Publication No. WO 04/018497, U.S. Patent Publication No. 2007/0166705A1, and U.S. Pat. No. 7,057, 026, each of which is incorporated herein by reference. For example, repeated cycles of SBS reagents can be delivered to a flow cell having target nucleic acids attached thereto, for example, as a result of the bridge amplification protocol. The nucleic acid clusters can be converted to single stranded form using a linearization solution. The linearization solution can contain, for example, a restriction endonuclease capable of cleaving one strand of each cluster. Other methods of cleavage can be used as an alternative to restriction enzymes or nicking enzymes, including inter alia chemical cleavage (e.g., cleavage of a diol linkage with periodate), cleavage of abasic sites by cleavage with endonuclease (for example the enzyme uracil-specific excision reagent 'USER®', an enzyme that generates a single nucleotide gap at the location of a uracil residue, as supplied by NEB, Ipswich, Mass., USA, part number M5505S), by exposure to heat or alkali, cleavage of ribonucleotides incorporated into amplification products otherwise comprised of deoxyribo-nucleotides, photochemical cleavage or cleavage of a peptide linker. After the linearization operation a sequencing primer can be delivered to the flow cell under conditions for hybridization of the sequencing primer to the target nucleic acids that are to be sequenced.

A flow cell can then be contacted with an SBS extension reagent having modified nucleotides with removable 3' blocks and fluorescent labels under conditions to extend a primer hybridized to each target nucleic acid by a single nucleotide addition. Only a single nucleotide is added to each primer because once the modified nucleotide has been incorporated into the growing polynucleotide chain complementary to the region of the template being sequenced there is no free 3'-OH group available to direct further sequence extension and therefore the polymerase cannot add further nucleotides. The SBS extension reagent can be removed and replaced with scan reagent containing components that protect the sample under excitation with radiation. Exemplary components for scan reagent are described in US publication US 2008/0280773 A1 and U.S. Ser. No. 13/018, 255, each of which is incorporated herein by reference. The extended nucleic acids can then be fluorescently detected in the presence of scan reagent. Once the fluorescence has been detected, the 3' block may be removed using a deblock reagent that is appropriate to the blocking group used. Exemplary deblock reagents that are useful for respective blocking groups are described in WO004018497, US 2007/ 0166705A1 and U.S. Pat. No. 7,057,026, each of which is incorporated herein by reference. The deblock reagent can be washed away leaving target nucleic acids hybridized to extended primers having 3' OH groups that are now competent for addition of a further nucleotide. Accordingly the cycles of adding extension reagent, scan reagent, and deblock reagent, with optional washes between one or more of the operations, can be repeated until a desired sequence is obtained. The above cycles can be carried out using a single extension reagent delivery operation per cycle when each of the modified nucleotides has a different label attached thereto, known to correspond to the particular base. The different labels facilitate discrimination between the nucleotides added during each incorporation operation. Alternatively, each cycle can include separate operations of extension reagent delivery followed by separate operations of scan reagent delivery and detection, in which case two or more of the nucleotides can have the same label and can be distinguished based on the known order of delivery.

Although the sequencing operation, at 106, has been exemplified above with respect to a particular SBS protocol, it will be understood that other protocols for sequencing any of a variety of other molecular analyses can be carried out as desired.

At 108, the one or more processors of the system receive the sequencing data for subsequent analysis at 110. The sequencing data may be formatted in various manners, such as in a .BAMS file. The sequencing data may include, for example, a number of sample reads. The sequencing data may include a plurality of sample reads that have corresponding sample sequences of the nucleotides. Although only one sample read is discussed, it should be understood that the sequencing data may include, for example, hundreds, thousands, hundreds of thousands, or millions of sample reads. Different sample reads may have different numbers of nucleotides. For example, a sample read may range between 10 nucleotides to about 500 nucleotides or more. The sample reads may span the entire genome of the source(s). As one example, the sample reads are directed toward predetermined genetic loci, such as those genetic loci having suspected STRs or suspected SNPs.

Each sample read may include a sequence of nucleotides, which may be referred to as a sample sequence, sample fragment or a target sequence. The sample sequence may include, for example, primer sequences, flanking sequences, and a target sequence. The number of nucleotides within the sample sequence may include 30, 40, 50, 60, 70, 80, 90, 100 or more. In some embodiments, one or more the sample reads (or sample sequences) includes at least 150 nucleotides, 200 nucleotides, 300 nucleotides, 400 nucleotides, 500 nucleotides, or more. In some embodiments, the sample reads may include more than 1000 nucleotides, 2000 nucleotides, or more. The sample reads (or the sample sequences) may include primer sequences at one or both ends.

At 110, the one or more processors analyze the sequencing data to obtain potential variant call(s) and a sample variant frequency of the sample variant call(s). The operation at 110 may also be referred to as a variant call application or variant caller. Alternative variant callers may be utilized in accordance with embodiments herein, wherein different variant callers may be used based on the type of sequencing operation being performed, based on features of the sample that are of interest and the like. One non-limiting example of a variant call application is the Pisces™ application by Illumina Inc. (San Diego, Calif.). Additionally or alternatively, the operation at 110 may utilize the variant call application described in the article "Strelka: accurate somatic small-variant calling from sequenced tumor-normal sample pairs" by Sanders et al., Bioformatics, 2012, July 15, Volume 28, No. 14, pages 1811-1817, the complete subject matter of which is expressly Incorporated herein by reference in its entirety.

In accordance with at least some embodiments, the variant call application at 110 provides calls for low frequency variants, germline calling and the like. As non-limiting example, the variant call application at 110 may run on tumor-only samples and/or tumor-normal paired samples. The variant call application at 110 may search for single nucleotide variations (SNV), multiple nucleotide variations (MNV), indels and the like. The variant call application identifies variants, while filtering for mismatches due to sequencing or sample preparation errors. For each variant, the variant caller identifies the reference sequence, a position of the variant, and the potential variant sequence(s) (e.g., A to C SNV, or AG to A deletion). The variant call application identifies the sample sequence (or sample fragment), a reference sequence/fragment, and a variant call as an indication that a variant is present. As explained hereafter in connection with FIG. 1B, the variant call application at 110 may identify raw fragments, and output a designation of the raw fragments, a count of the number of raw fragments that verify the potential variant call, the position within the raw fragment at which a supporting variant occurred and other relevant information. Non-limiting examples of raw fragments include a duplex stitched fragment, a simplex stitched fragment, a duplex un-stitched fragment and a simplex un-stitched fragment.

The variant call application may output the calls in various formats, such as in a .VCF or .GVCF file. By way of example only, the variant call application may be included in a MiSeqReporter pipeline (e.g., when implemented on the MiSeq® sequencer instrument). Optionally, the application may be implemented with various workflows. The analysis, at 110, may include a single protocol or a combination of protocols that analyze the sample reads in a designated manner to obtain desired information.

At 111, the one or more processors perform a validation operation in connection with the potential variant call. The validation operation as described below in more detail in connection with FIGS. 1C-5B. The validation operation may be based on a quality score, and/or a hierarchy of tiered tests, as explained hereafter. When the validation operation authenticates or verifies that the potential variant call, the validation operation passes the variant call information (from the variant call application at 110) to the sample report generator at 112. Alternatively, when the validation operation invalidates or disqualifies the potential variant call, the validation operation passes a corresponding indication (e.g., a negative indicator, a no call indicator, an in-valid call indicator) to the sample report generator at 112. The validation operation at 111 also may pass a confidence score related to a degree of confidence that the variant call is correct or the in-valid call designation is correct.

At 112, the one or more processors generate and store a sample report. The sample report may include, for example, information regarding a plurality of genetic loci with respect to the sample. For example, for each genetic locus of a predetermined set of genetic loci, the sample report may at least one of provide a genotype call; indicate that a genotype call cannot be made; provide a confidence score on a certainty of the genotype call; or indicate potential problems with an assay regarding one or more genetic loci. The sample report may also indicate a gender of an individual that provided a sample and/or indicate that the sample include multiple sources. As used herein, a "sample report" may include digital data (e.g., a data file) of a genetic locus or predetermined set of genetic locus and/or a printed report of the genetic locus or the set of genetic loci. Thus, generating or providing, at 112, may include creating a data file and/or printing the sample report, or displaying the sample report.

The sample report may indicate that a variant call was determined, but was not validated. When a variant call is determined in-valid, the sample report may indicate additional information regarding the basis for the determination to not validate the variant call. For example, the additional information in the report may include a description of the raw fragments and an extent (e.g., a count) to which the raw fragments support or contradicted the variant call. Additionally or alternatively, the additional information in the report may include the quality score obtained in accordance with embodiments described herein.

Variant Call Application

Figure 1B:
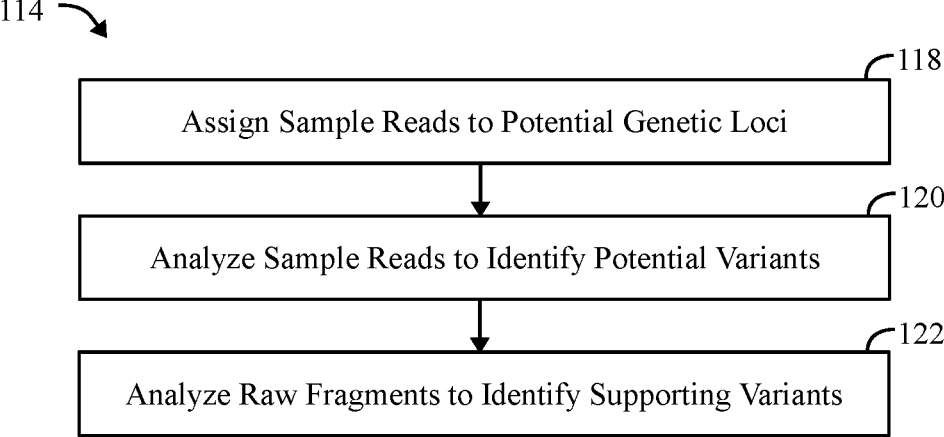
FIG. 1B illustrates a flowchart for a method for analyzing sequencing data to identify potential variant calls in accordance with an embodiment herein.

FIG. 1B illustrates a flowchart for a method 114 for analyzing sequencing data to identify potential variant calls in accordance with an embodiment herein. By way of example, the operations of FIG. 1B may be performed during 110 in FIG. 1A. It is understood that the operations of FIG. 1B may operate upon stored data for a previously performed sequencing operation. Additionally or alternatively, the operation of FIG. 1B may be performed in real time while a sequencing operation is being performed. At 118, each of the sample reads is assigned to corresponding genetic loci. The sample reads may be assigned to corresponding genetic loci based on the sequence of the nucleotides of the sample read or, in other words, the order of nucleotides within the sample read (e.g., A, C, G, T). Based on this analysis, the sample read may be designated as including a possible variant/allele of a particular genetic locus. The sample read may be collected (or aggregated or binned) with other sample reads that have been designated as including possible variants/alleles of the genetic locus. The assigning operation, at 118, may also be referred to as a calling operation in which the sample read is identified as being possibly associated with a particular genetic position/ locus. The sample reads may be analyzed to locate one or more identifying sequences (e.g., primer sequences) of nucleotides that differentiate the sample read from other sample reads. More specifically, the identifying sequence(s) may identify the sample read from other sample reads as being associated with a particular genetic locus.

The assigning operation, at 118, may include analyzing the series of n nucleotides of the identifying sequence to determine if the series of n nucleotides of the identifying sequence effectively matches with one or more of the select sequences. In particular embodiments, the assigning operation, at 118, may include analyzing the first n nucleotides of the sample sequence to determine if the first n nucleotides of the sample sequence effectively matches with one or more of the select sequences. The number n may have a variety of values, which may be programmed into the protocol or entered by a user. For example, the number n may be defined as the number of nucleotides of the shortest select sequence within the database. The number n may be a predetermined number. The predetermined number may be, for example, 10, 11, 12, 13, 14, 15, 16, 17, 18, 19, 20, 21, 22, 23, 24, 25, 26, 27, 28, 29, or 30 nucleotides. However, fewer or more nucleotides may be used in other embodiments. The number n may also be selected by an individual, such as a user of the system. The number n may be based on one or more conditions. For instance, the number n may be defined as the number of nucleotides of the shortest primer sequence within the database or a designated number, whichever is the smaller number. In some embodiments, a minimum value for n may be used, such as 15, such that any primer sequence that is less than 15 nucleotides may be designated as an exception.

In some cases, the series of n nucleotides of an identifying sequence may not precisely match the nucleotides of the select sequence. Nonetheless, the identifying sequence may effectively match the select sequence if the identifying sequence is nearly identical to the select sequence. For example, the sample read may be called for a genetic locus if the series of n nucleotides (e.g., the first n nucleotides) of the identifying sequence match a select sequence with no more than a designated number of mismatches (e.g., 3) and/or a designated number of shifts (e.g., 2). Rules may be established such that each mismatch or shift may count as a difference between the sample read and the primer sequence. If the number of differences is less than a designated number, then the sample read may be called for the corresponding genetic locus (i.e., assigned to the corresponding genetic locus). In some embodiments, a matching score may be determined that is based on the number of differences between the identifying sequence of the sample read and the select sequence associated with a genetic locus. If the matching score passes a designated matching threshold, then the genetic locus that corresponds to the select sequence may be designated as a potential locus for the sample read. In some embodiments, subsequent analysis may be performed to determine whether the sample read is called for the genetic locus.

If the sample read effectively matches one of the select sequences in the database (i.e., exactly matches or nearly matches as described above), then the sample read is assigned or designated to the genetic locus that correlates to the select sequence. This may be referred to as locus calling or provisional-locus calling, wherein the sample read is called for the genetic locus that correlates to the select sequence. However, as discussed above, a sample read may be called for more than one genetic locus. In such embodiments, further analysis may be performed to call or assign the sample read for only one of the potential genetic loci. In some embodiments, the sample read that is compared to the database of reference sequences is the first read from paired-end sequencing. When performing paired-end sequencing, a second read (representing a raw fragment) is obtained that correlates to the sample read. After assigning, at 118, the subsequent analysis that is performed with the assigned reads may be based on the type of genetic locus that has been called for the assigned read.

At 120, the sample reads are analyzed to identify potential variant calls. Among other things, the results of the analysis identify the potential variant call, a sample variant frequency, a reference sequence and a position within the genomic sequence of interest at which the variant occurred. For example, if a genetic locus is known for including SNPs, then the assigned reads that have been called for the genetic locus may undergo analysis, at 120, to identify the SNPs of the assigned reads. If the genetic locus is known for including polymorphic repetitive DNA elements, then the assigned reads may be analyzed, at 120, to identify or characterize the polymorphic repetitive DNA elements within the sample reads. In some embodiments, if an assigned read effectively matches with an STR locus and an SNP locus, a warning or flag may be assigned to the sample read. The sample read may be designated as both an STR locus and an SNP locus. The analyzing, at 120, may include aligning the assigned reads in accordance with an alignment protocol to determine sequences and/or lengths of the assigned reads. The alignment protocol may include the method described in International Application No. PCT/US2013/030867 (Publication No. WO 2014/142831), filed on Mar. 15, 2013, which is herein incorporated by reference in its entirety.

At 122, the one or more processors analyze raw fragments to determine whether supporting variants exist at corresponding positions within the raw fragments. Various types of raw fragments may be identified. For example, the variant caller may identify a type of raw fragment that exhibits a variant that validates the original variant call. For example, the type of raw fragment may represent a duplex stitched fragment, a simplex stitched fragment, a duplex un-stitched fragment or a simplex un-stitched fragment. Optionally other raw fragments may be identified instead of or in addition to the foregoing examples. In connection with identifying each type of raw fragment, the variant caller also identifies the position, within the raw fragment, at which the supporting variant occurred, as well as a count of the number of raw fragments that exhibited the supporting variant. For example, the variant caller may output an indication that 10 reads of raw fragments were identified to represent duplex stitched fragments having a supporting variant at a particular position X. The variant caller may also output indication that five reads of raw fragments were identified to represent simplex un-stitched fragments having a supporting variant at a particular position Y. The variant caller may also output a number of raw fragments that corresponded to reference sequences and thus did not include a supporting variant that would otherwise provide evidence validating the potential variant call at the genomic sequence of interest.

At 122, a count is maintained of the raw fragments that include supporting variants, as well as the position at which the supporting variant occurred. Additionally or alternatively, a count may be maintained of the raw fragments that did not include supporting variants at the position of interest (relative to the position of the potential variant call in the sample read or sample fragment). Additionally or alternatively, a count may be maintained of raw fragments that correspond to a reference sequence and do not authenticate or confirm the potential variant call. The information determined at 122 is output to the variant call validation application, including a count and type of the raw fragments that support the potential variant call, positions of the supporting variance in the raw fragments, a count of the raw fragments that do not support the potential variant call and the like.

When a potential variant call is identified, the process of FIG. 1B outputs an indicating of the potential variant call, the variant sequence, the variant position and a reference sequence associated therewith. The variant call is designated to represent a "potential" variant as errors may cause the call process to identify a false variant. In accordance with embodiments herein, the potential variant call is analyzed to reduce and eliminate false variants or false positives. Additionally or alternatively, the process of FIG. 1B analyzes one or more raw fragments associated with a sample read and outputs a corresponding variant call associated with the raw fragments.

Variant Call Validation Application

Figure 1C:
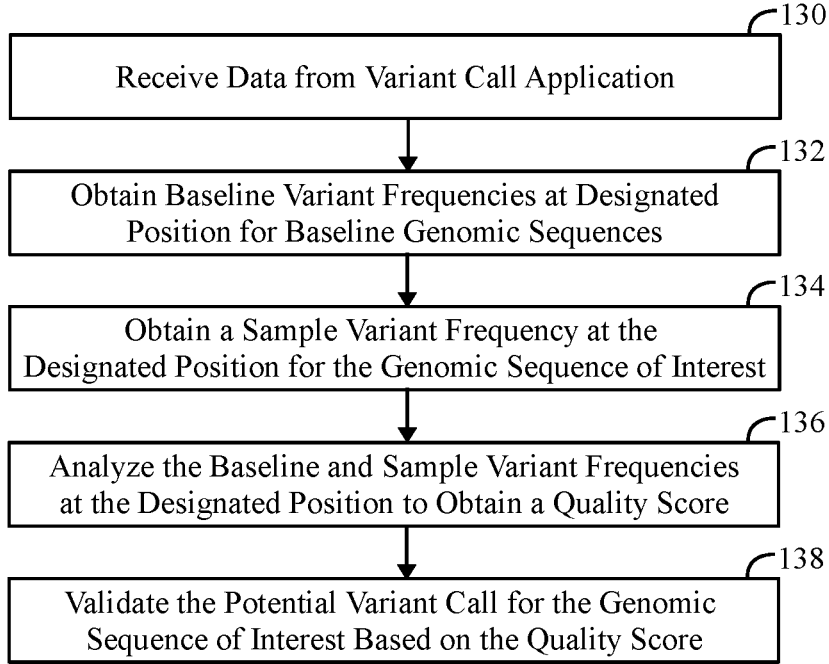
FIG. 1C illustrates a computer implemented method for validating variant calls in accordance with embodiments herein.

FIG. 1C illustrates a computer implemented method for validating variant calls in accordance with embodiments herein. At 130, the one or more processors receives data from the variant call application (FIG. 1B) including an indication of the potential variant call at a designated position, a position of the potential variant call within the genomic sequence of interest. At 130, the one or more processors also receive a count and type of the raw fragments that support the potential variant call, positions of the supporting variants in the raw fragments, a count of the raw fragments that do not support the potential variant call and other relevant information. It is understood that the operation at 130 may correspond to one or more operations to access stored data for a previously performed sequence. Additionally or alternatively, the operation at 130 may be performed in real time while a sequencing operation is being performed.

Optionally, at 130, the one or more processors may receive an indication of a reference sequence, with respect to which the potential variant call was made. The reference sequence corresponds to a sequence of nucleotides within one or more baseline genomic sequence(s).

Figure 1D:
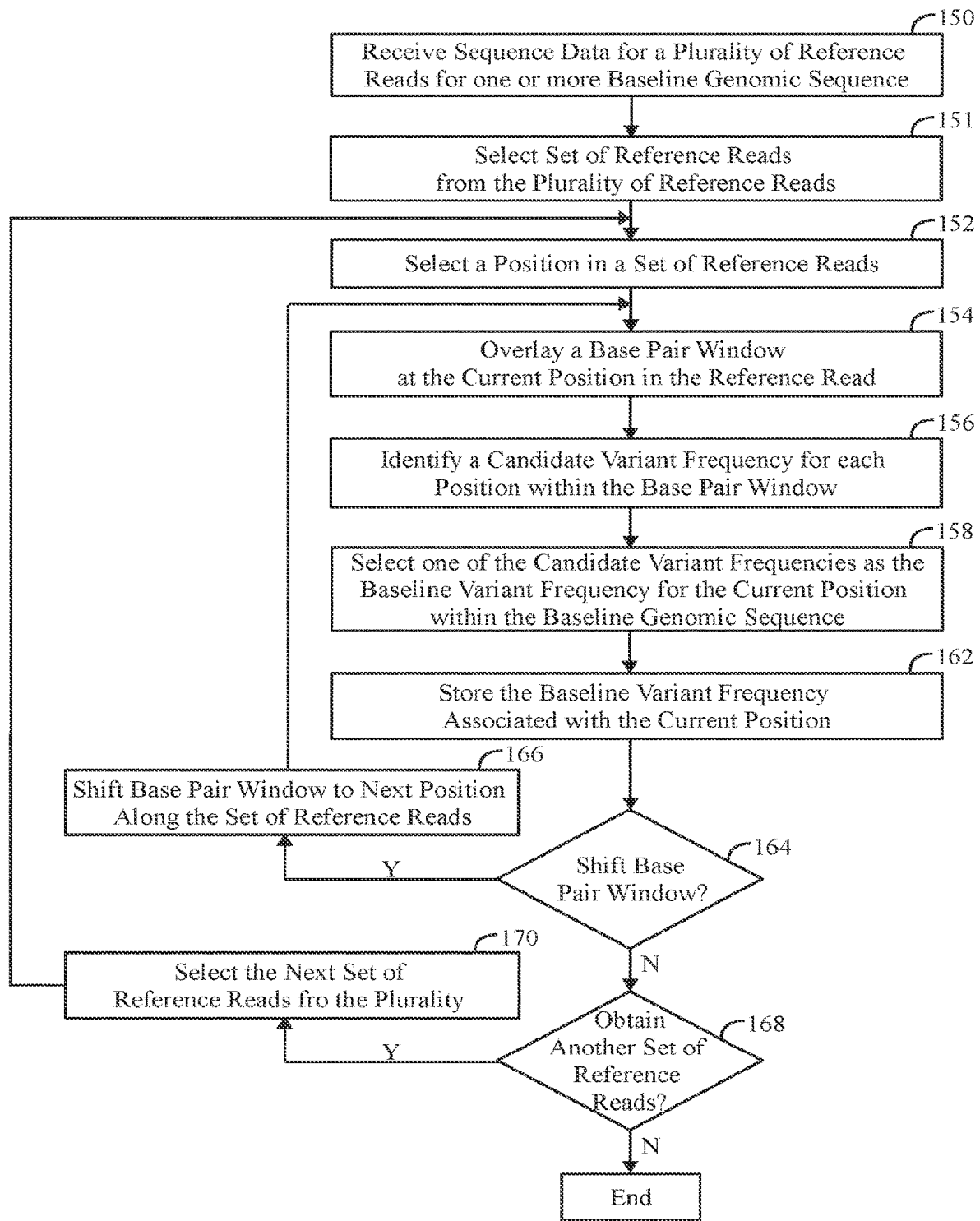
FIG. 1D illustrates a process for obtaining baseline variant frequencies in accordance with embodiments herein.

At 132, the one or more processors obtain one or more baseline variant frequencies at the designated position within one or more baseline genomic sequences (e.g., in accordance with the process of FIG. 1D). As one example, the baseline variant frequencies are derived from multiple baseline genomic sequences that are associated with more than one type of allele. Optionally, the baseline variant frequencies may be associated with one type of allele, but derived from samples from multiple individuals. The baseline variant frequencies may be determined at the same time as the other operations of FIG. 1C. Alternatively, the baseline variant frequencies may be predetermined prior to implementation of a sequencing operation for a sample of interest or the validation process of FIG. 1C. The baseline variant frequencies may be stored (e.g., in a library or database) in connection with various positions along various reference baseline genomic sequences. For example, a library or database may be maintained for multiple baseline genomic sequences. The library or database (e.g., 784 in FIG. 7) may also retain baseline variant frequencies associated with each position along the baseline genomic sequence. It is recognized that a baseline genomic sequence may exhibit different types of baseline variant frequencies, such as in connection with different types of sequencing methods, preparation methods, sequencing equipment and the like. Accordingly, the library or database may maintain a set of baseline variant frequencies for any given position along a baseline genomic sequence. The operation at 132 may include sending a request to a network server or remote computer (e.g., 780) that manages a library or database. The request may designate the baseline genomic sequence of interest, the designated position there along, as well as additional information (e.g., the type of sequencing operation, the type of equipment being used, or the library preparation protocol).

The baseline variant frequencies may be determined in different manners to identify different characteristics of interest describing variation at one or more positions along the baseline genomic sequence. By way of example, the baseline variant frequencies indicate a degree (or an extent) of background noise at corresponding positions along the baseline genomic sequence. The degree/extent of background noise may vary, for example depending upon the type of sequencing operation, type of equipment, library preparation process and the like.

At 134, the one or more processors obtain the sample variant frequency at the designated position for the genomic sequence of interest. For example, the processors obtains the sample variant frequency from the variant call application, where the sample variant frequency represents a relative frequency of an allele (variant of a gene) at a particular position/locus in a genomic sequence of interest across a population of samples. For example, the sample variant frequency may be expressed as a fraction or percentage of all samples of interest (e.g., chromosomes) from the individual that were analyzed.

At 136, the one or more processors analyzes the baseline and sample variant frequencies at the designated position to obtain a quality score. By way of example, the analysis may include obtaining a relation between the sample variant frequency and a distribution of the baseline variant frequencies, with the quality score being determined based on the relation. For example, multiple baseline variant frequencies may be stored for a population of baseline genomic sequences. The multiple baseline variant frequencies are organized into a distribution. The processors may index the sample variant frequency with respect to the distribution of the baseline variant frequencies. As one example, the relation may be based on a non-parametric test, such as a Wilcoxon rank sum test. The Wilcoxon rank sum test produces a p-value representing a relation between the sample variant frequency and the distribution of the baseline variant frequencies. The p-value represents a numeric indication of a degree of confidence that a sample variant call is due to noise or not due to background noise.

The processors convert the numeric p-value to a quality score (e.g., referred to as a Q-score). For example, the quality score may simply equal the p-value. Alternatively, the quality score may be formed by applying a predetermined mathematical operator to the p-value (e.g., normalize the p-value, convert the p-value to a whole number). Optionally, the p-value may be combined with other information/factors to form the quality score. For example, the p-value may be modified based on a number of samples and/or sample reads obtained. Optionally, alternative tests may be applied to determine a relation between the baseline variant frequencies and the sample variant frequency, where such alternative tests afford an indication of a degree of confidence in a sample variant call. For example, the degree of confidence may indicate that the sample variant call is due to background noise or not due to background noise. Alternatively, the degree of confidence may indicate that the sample variant call includes various types of systematic errors that cause false variants, such as due to FFPE artifacts, sequencing errors or PCR errors.

At 138, the one or more processors validate the potential variant call for the genomic sequence of interest based on the quality score. By way of example, the validation operation may further comprise comparing the quality score to a threshold and declaring the potential variant call to be a valid variant call when the quality score exceeds the threshold. The threshold represents a Q-score cut-off to filter out potential false variants. A valid variant call may represent a variant call for which a "high" confidence exists that the call is accurate. The measure of what represents high confidence, versus low confidence is recognized to represent a relative term that may vary based on the particular facts and circumstances of the implementation. As one example, the threshold may be varied based on empirical analysis.

FIG. 1D illustrates a process for obtaining baseline variant frequencies in accordance with embodiments herein. The process of FIG. 1D may be carried out by one or more processors of various systems and devices. It is understood that the order in which the operations of FIG. 1D represent one example, while the operations may be performed in alternative orders. Further, one or more of the operations of FIG. 1D may be omitted entirely. The operations of FIG. 1D will be described in connection with FIG. 2.

The method of FIG. 1D may be repeated periodically to compile a locus specific background error distribution from a plurality of panels for FFPE normal samples with varied DNA quality from various tissues sequenced by a NGS-based assay. The method of FIG. 1D may utilize the same sequencing data from the plurality of panels of the FFPE normal samples to normalize systematic bias in read coverage caused by PCR, DNA quality, probe pull-down efficiency, or sequence GC content to reveal an accurate number of variants in a test sample.

Figure 2A:
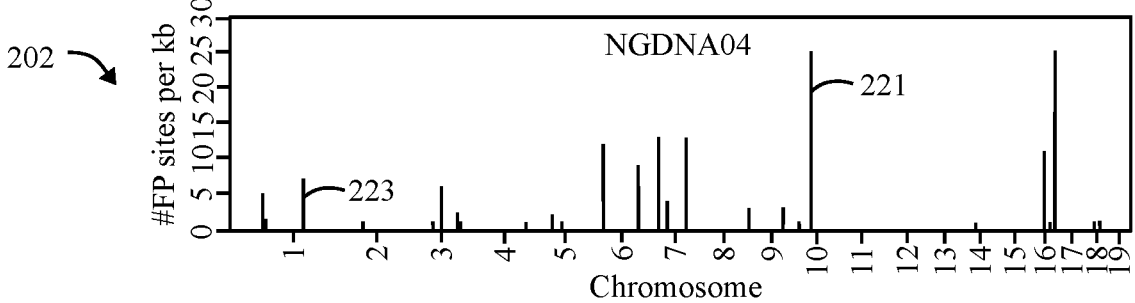
FIG. 2A illustrates example panels for different individuals within a baseline population utilized in accordance with embodiments herein.
Figure 2A:
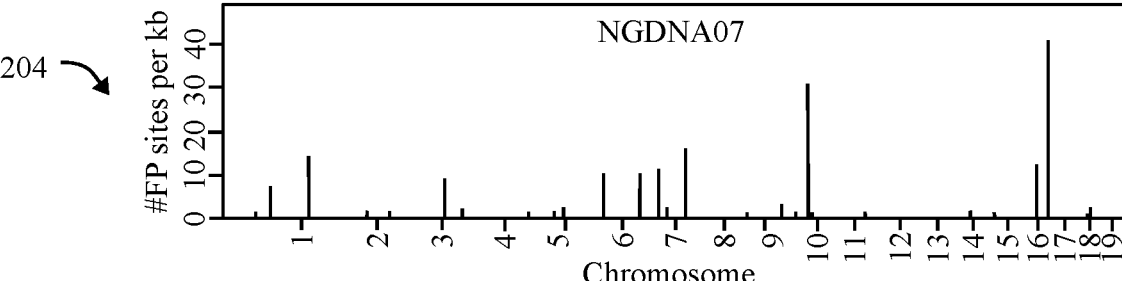
Figure 2A:
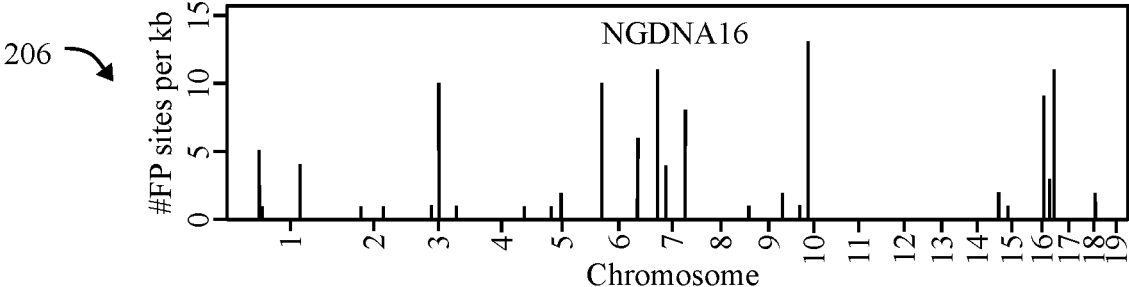

FIG. 2A illustrates example panels 202-206 for different individuals within a baseline population. In the present example, the baseline population represent normal/healthy individuals, although, it is recognized that the baseline population may represent individuals that exhibit a particular mutation of interest, such as a particular type of cancer and the like. The vertical axis of the panels 202-206 represents the number of false positive or false variant calls found per 1000 bases analyzed. It is understood that each panel 202-206 corresponds to an accumulation of a large number of reference reads, for example 1000, 5000, 10,000 and the like. The horizontal axis indicates all or a portion of the chromosomes within a baseline genomic sequence. In the example of FIG. 2, 19 chromosomes are illustrated along the baseline genomic sequence, although it is understood that the baseline genomic sequence may be maintained for more or fewer chromosomes. A series of vertical bars are designated along the horizontal axis, with each bar extending upward by an amount corresponding to the number of false variants at the corresponding position or site along the corresponding chromosome. The vertical bars are positioned along the horizontal axis at approximate locations of the corresponding position or coordinate within the associated chromosome. For example, a vertical bar 221 is presented in connection with the $10^{th}$ chromosome to indicate that the $10^{th}$ chromosome experienced approximately 25 false variants per 1000 Bases, where the position or coordinate within the chromosome is slightly below the center of the chromosome. As another example, a vertical bar 223 is presented in connection with the first chromosome to indicate that the first chromosome experienced approximately 7 false variants per 1000 Bases at a position or coordinate slightly above the center of the first chromosome.

Figure 2B:
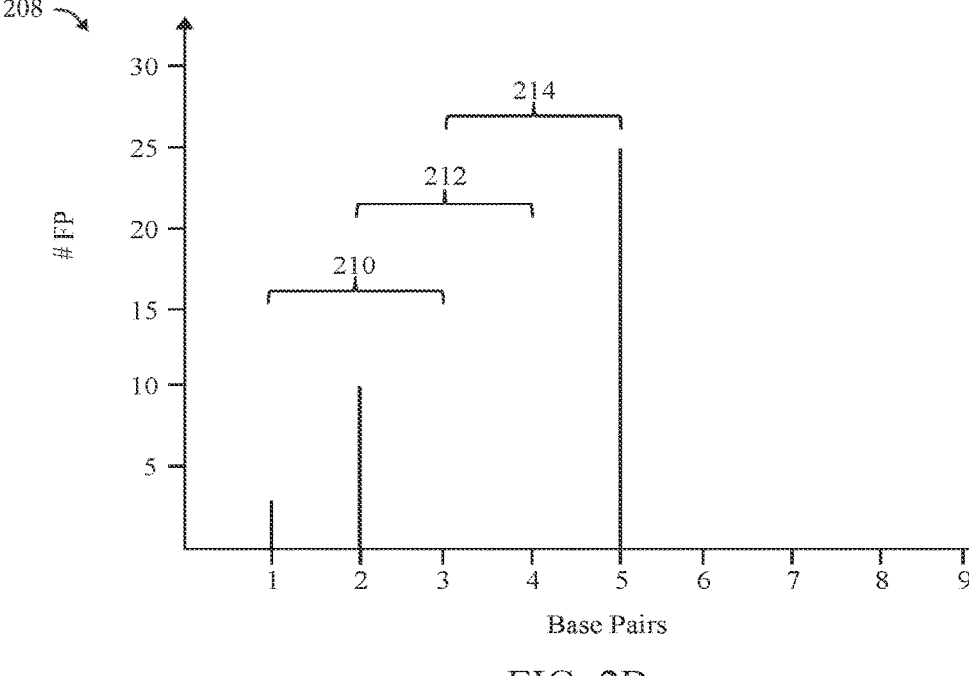
FIG. 2B illustrates a base pair panel representing an enlargement for a small portion of one of the panels of FIG. 2A.

FIG. 2B illustrates a base pair panel representing an enlargement for a small portion of one of the panels 202-206 of FIG. 2A. By way of example, FIG. 2B may correspond to a reference reads for base pairs 1-9 in chromosome 16 of panel 202 (FIG. 2A). The base pair panel 208 includes a vertical axis that represents the number of false variant calls found per 1000 bases analyzed. As explained above in connection with FIG. 2A, the base pair panel 208 corresponds to an accumulation of a large number of reference reads, for example 1000, 5000, 10,000 and the like. The horizontal axis indicates a short sequence of base pairs associated with a single chromosome within a baseline genomic sequence. In the example of FIG. 2B, 9 base pairs are illustrated along the baseline genomic sequence, although it is understood that the baseline genomic sequence is maintained for more base pairs for the present and other chromosomes. A series of vertical bars are designated along the horizontal axis, with each bar extending upward by an amount corresponding to the number of false variants at the corresponding base pair position or site along the corresponding chromosome. The vertical bars are positioned along the horizontal axis at locations of the corresponding base pair within the associated chromosome. For example, a vertical bar is presented at base pair #2 to indicate that the base pair #1 experienced approximately 10 false variants per 1000 Bases. As another example, a vertical bar is presented in connection with base pair #5 to indicate that base pair #5 experienced approximately 25 false variants per 1000 Bases.

Returning to FIG. 1D, at 150, the one or more processors receive sequence data for a plurality of reference reads for one or more baseline genomic sequences. With respect to FIG. 2A, if it is assumed that each of the panels 202-206 represents an accumulation of 1000 reference reads, then the system would obtain about 3000 reference reads. At 151, the one or more processors select a set of the reference reads from the plurality of reference reads. With respect to FIG. 2A, the set of reference reads may be selected corresponding to base pair 1-9 in chromosome 16 for the individual designated as WGDNA04 (panel 202). FIG. 2B illustrates an example for base pairs 1-9 in chromosome 16. At 152, the one or more processors of the system select a current position in the current set of reference reads. For example, the current position may be centered at position #2 along the panel 208. At 154, the one or more processors of the system overlay the current position in the set of reference reads with a base pair window.

In FIG. 2B, a bracket 210 is presented to illustrate an example of a base pair window. The length of the base pair window may be varied, for example ranging from one base pair to any desired number of multiple base pairs. In the example of FIG. 2B, the base pair window has been designated to correspond to three base pairs, although other lengths may be utilized. Accordingly, at the present iteration through the operations of FIG. 1D, the base pair window 210 encompasses positions #1-#3. Utilizing a base pair window that covers more than one base pair accounts for the circumstance in which noising positions may occur together. For example, when library preparation or other factors cause noise to occur at one position in a nucleotide sequence, the same factors may cause noise to occur at one or more positions adjacent to the one position. The length of the base pair window may be defined in part based on the extent to which noise is expected to span across multiple base pair positions.

At 156, the one or more processors identify a candidate variant frequency for each position of the reference reads within the base pair window. Continuing with the foregoing example, a candidate variant frequency would be identified for each of the positions #1-#3 within the base pair window 210 (e.g., about 2 false variants at #1, about 10 false variant at position #2, and about 0 false variants at position #3).

At 158, the one or more processors select one of the candidate variant frequencies to represent the baseline variant frequency (also referred to as the resultant variant frequency) for the current position within the baseline genomic sequence. For example, the current position may correspond to the center of base pair window 210. Alternatively, the current position may correspond to the leading edge or trailing edge of the base pair window 210. The selection for the baseline/resultant variant frequency may be based on various criteria. For example, the processors may select the highest candidate variant frequency within the base pair window. Alternatively, the processors may form a mathematical combination of the candidate variant frequencies, such as through averaging, a weighted sum or the like, to form the baseline/resultant variant frequency. The baseline/resultant variant frequency is stored in connection with the current base pair position. For example, the baseline/resultant variant frequency may be stored in the baseline genomic sequence database (784 in FIG. 7). With reference to FIG. 2B, the base pair window 210 may be assigned the baseline variant frequency of 10 (corresponding to the highest variant frequency within the window).

At 162, the one or more processors of the system store the baseline variant frequency in connection with the current position. The baseline variant frequency may be recorded, relative to the current position, in different manners. The variant frequency for base pair #1 and a base pair #3 (both within the window 210) may be left unchanged. With respect to FIG. 2B, the baseline variant frequency value of 10 may be recorded in connection with base pair positioned #2.

Alternatively, the baseline variant frequency may be assigned to the leading position #1 or trailing position #3 within the base pair window, while the adjacent positions are assigned a null value or left unchanged. Optionally, the baseline variant frequency may be assigned to each position within the base pair window.

Optionally, the baseline variant frequency may be set to a predefined level, where different predefined levels are utilized in connection with different candidate variant frequencies. For example, when the candidate variant frequencies are relatively high (e.g., above about 30%), the baseline variant frequency may be set to zero or another predefined lower level. By way of example, the baseline variant frequency may be set to zero or a predefined level, when candidate variant frequencies exceed a threshold to avoid counting germ like variant as background noise.

At 164, the one or more processors determine whether to shift the base pair window to another position along the current set of reference reads. The determination to shift the base pair window may be based on whether an additional portion of the reference read remains to be analyzed. When the decision at 164 is to shift the base pair window, flow moves to 166. Otherwise, flow continues to 168.

At 166, the one or more processors of the system shift the base pair window to a next position along the set of reference reads, and flow returns to 154. Thereafter, the operations at 154 and 156 are repeated. By way of example, the shift at 166 may shift the base pair window by a single base pair, or by multiple base pair. For example, with reference to FIG. 2B, the shift may correspond to a single base pair. Thus, the base pair window is shifted from the position designated at bracket 210 to the position designated at bracket 212 (covering base pair positions #2-#4). During a subsequent iteration through the operations at 164-166, the base pair window may be shifted from the position designated at 212 to the position designated at 214 (covering base pair positions #3-#5).

In the present example, the base pair window is shifted to successive overlapping positions. When the base pair window includes more than 3 base pairs, the shift at 166 may similarly be greater than 1 base pair. For example, if the base pair window is 5 base pair long and the current position corresponds to window (positions #1-#5), at 166, the base pair window may be shifted forward 2 position to overlap positions #3-#7, such that successive positions of the base pair window are overlapping, but stepping forward by multiple base pair between successive base pair windows.

Alternately, the base pair window may be shifted to successive non-overlapping positions along the reference read. For example, if the base pair window is 3 base pair long and the current position corresponds to positions #1, #2 and #3 in the set of reference reads, at 166, the base pair window may be shifted forward 3 positions to overlap positions #4, #5 and #6, such that successive positions of the base pair window are non-overlapping.

Next, the operations at 154-162 are repeated for the next position. When flow advances from 164 to 168, the one or more processors of the system determines whether additional sets of reference reads are to be analyzed from the plurality of reference reads. When additional reference reads are to be analyzed, flow returns to 170. Otherwise, the process of FIG. 1D ends and flow returns to FIG. 1C. At 170, the one or more processors select the next set of reference reads to be analyzed. Thereafter, flow returns to 152. The operations at 152-166 are then repeated.

Figure 3:
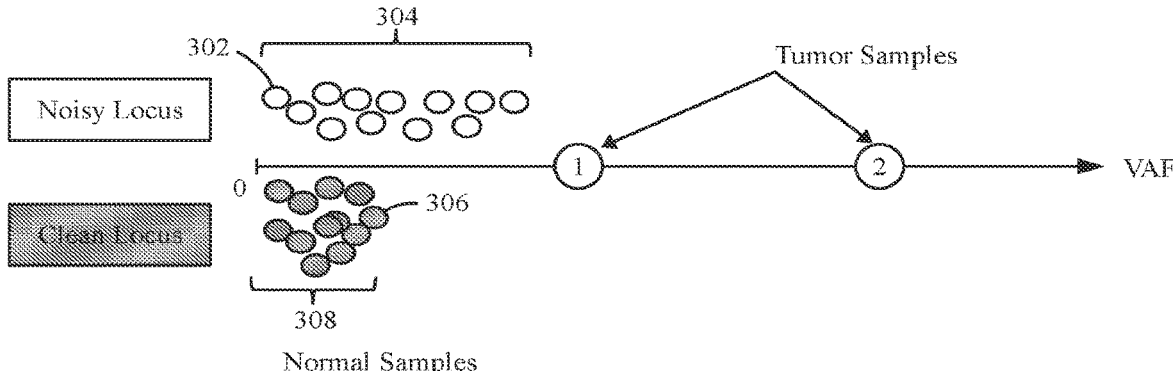
FIG. 3 illustrates a graphic in connection with the principle of background correction utilizing normal baseline genomic sequences in accordance with embodiments herein.

FIG. 3 illustrates a graphic in connection with the principle of background correction utilizing normal baseline genomic sequences. The horizontal axis represents variant allele frequencies (VAF) which corresponds to the frequency of variation in a sample at some designated position along a nucleotide sequence. Each circle 302 represents a variant associated with a sample, while the cluster 304 of variants 302 correspond to a position along a genomic sequence for a cluster of samples. The cluster 304 exhibits a relatively large amount of noise (also referred to as a noisy locus) across the baseline population. Circles 306 also represent a variant associated with a different sample, while the cluster 308 corresponds to a position along a genomic sequence for a cluster of samples. The cluster 308 exhibits a relatively small amount of noise (also referred to as a clean locus) across the baseline population.

The method of FIG. 1D develops a profile for the background noise for a population of normal samples by collecting the variant frequencies at positions of interest along the genomic sequence of interest. The background population exhibits a "clean locus" where allele frequency is relatively tightly/closely distributed in an area near zero, such as in cluster 308. Accordingly, a tumor variant call (with an individual being tested) can be easily differentiated from noise even when the allele frequency for the sample genomic sequence of interest is low (e.g., at tumor sample number 1). Alternatively, the background population may exhibit a "noisy locus" where allele frequency is more widely distributed/spread out at various points of interest along the genomic sequence of interest, such as in cluster 304. Accordingly, it may be more difficult to differentiate a tumor variant call (for a sample of interest) that exhibits a low variant frequency (e.g., such as tumor sample 1) from background noise. Although, a high frequency variant call (e.g., such as tumor sample 2) can still be called confidently, regardless of whether the position of interest exhibits clean or noisy background characteristics. Embodiments herein utilize the background noise level of normal samples to adjust calling stringency in connection with tumor samples.

Next, aspects of embodiments herein are described in connection with utilizing information from the foregoing processes and information from raw fragments to improve variant calling sensitivity and specificity.

Figure 4:
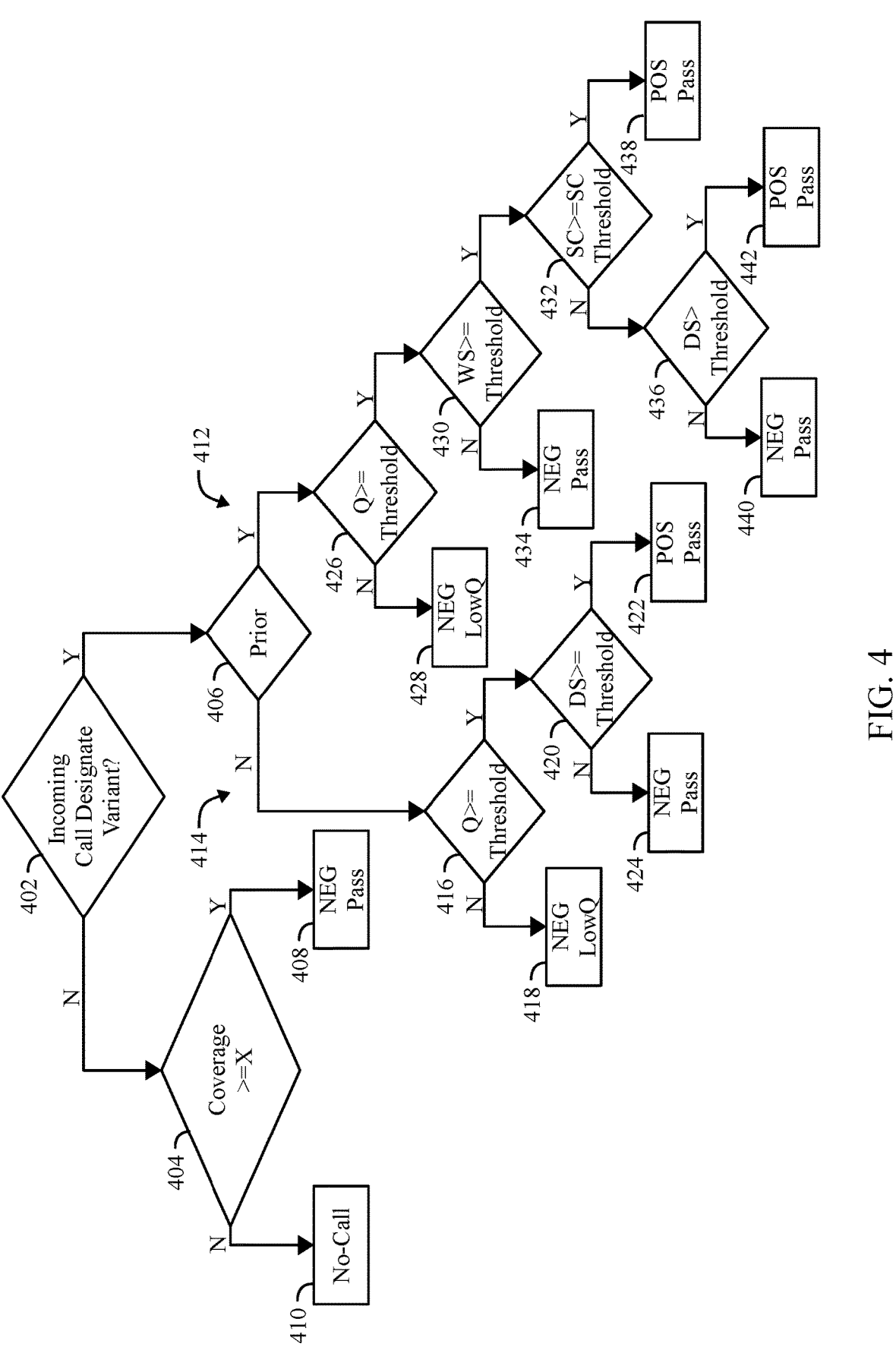
FIG. 4 illustrates a hierarchy-based decision tree to filter variant calls implemented in accordance with embodiments herein.

FIG. 4 illustrates a hierarchy-based decision tree implemented in accordance with embodiments herein to filter variant calls. At 402, one or more processors determine whether an incoming call indicates a variant (allele) has been observed. When no variant is observed, this may represent that the call has been identified to correspond to a reference sequence without any variant. When an incoming call is indicated to correspond to a reference sequence, flow branches to 404. Otherwise, when an incoming call is indicated to include a variant/allele, flow branches to 406.

At 404, the one or more processors determine whether a predetermined amount of coverage has been obtained for the current variant/allele. Coverage may be determined based on an indication of a number of reads that have been collected covering a fragment of a genome sequence of interest that includes a current position/locus. The coverage may be defined in various manners. For example, coverage may be defined based on a number of molecules that have been analyzed to obtain reads for the current position/locus. Additionally or alternatively, coverage may be defined based on a number of samples, from which reads have been obtained for the current position/locus. At 404, a coverage threshold is defined (e.g., 10×, 100×, etc.). When the number of reads, that include the current locus, exceeds the coverage threshold, flow advances to 408 where a "negative pass" is declared. The "negative pass" indicates that the process validates the incoming call in the original form (e.g., verifies the negative call). For example, when the incoming call identifies a sample sequence to correspond to a particular reference sequence, at 408, the process passes the call without modification.

Otherwise, when the processors determine that the coverage does not equal or exceed the coverage threshold, flow advances to 410 where a "no call" condition is designated. A no call condition is designated when the coverage of the present locus is too low to exhibit sufficient confidence that a "no variant call" is accurate. Therefore, the incoming call is changed to a "no call", such as to provide no indication of any correlation of the sample sequence to any reference sequence. Reference calls below a certain coverage cutoff are filtered to avoid declaring no variant due to a variant-carrying read at low depth.

At 406, the one or more processors determine whether the current variant corresponds to a prior variant. For example, the current variant may be compared to a collection of variants (in the prior database 782 in FIG. 7) which stores information regarding common variants exhibited across a population. For example, information from known databases (e.g., 1000G phase 3 and Cosmic database) may be used to increase confidence in variant calls that are known to occur in the population. When the current variant is similar to a prior variant in the prior variants database, flow moves along branch 412, where a series of hierarchy based tiered tests are performed. At 406, when no prior variant is identified from a database, flow moves along branch 414, where a different series of hierarchy based tiered tests are performed. One or more of the tiered test may be performed along each of the branches 412 and 414. Further, the various tests may be performed in alternative orders and in alternative combinations other than the particular arrangement illustrated in FIG. 4. Each of the tests in FIG. 4 provide a corresponding degree/level of secondary supporting evidence that a variant has or has not occurred, with the tests exhibiting different degrees of confidence as secondary supporting evidence.

Following branch 414, at 416, the one or more processors determine whether a variant quality score for the current variant exceeds a quality score threshold. The variant quality score is determined in accordance with embodiments herein, such as described in connection with FIGS. 1C and 1D. As explained herein, the variant quality score represents a relation between a sample variant frequency and multiple baseline variant frequencies. When the variant quality score is less than the quality score threshold, flow moves to 418 where the current variant is invalidated, such as designated as a false variant (e.g., declaring the call to represent a "negative" due to a low quality score). When the variant quality score is equal to or greater than the quality score threshold, flow moves to 420.

At 420, the one or more processors obtains and reviews a count of duplex fragments (e.g., duplex stitched or un-stitched) that support a variant call. The count indicates a number of duplex raw fragments that were identified by the variant call application to obtain a supporting variant corresponding the potential variant in the sample read. During sequencing, both strands of DNA are analyzed and reads are obtained for fragments from each strand. By way of example, at least first and second reads may be obtained for overlapping fragments of the first strand, while third and fourth reads are obtained for fragments of the second strand. The set of 1-4 reads are reviewed to determine how many of the reads indicate a variant at the current position/locus.

When a variant is present in a sample read, it would be expected that all of the reads for the current locus in each of the first and second strands would exhibit a related or "supporting" variant. For example, when the sample read corresponds to a first strand and is called for a potential variant (e.g., a locus exhibits an "A"), the corresponding locus in the second strand (corresponding to the raw fragment) would be expected to be a "T". When the corresponding locus in the second strand (raw fragment) includes a variant that is a "T", the current read of the raw fragment would be counted to have a supporting variant. If a matching supporting variant occurs in each of the strands (sample fragment read and raw fragment read) within a double stranded DNA, this may be considered a good indicator that a variant has occurred at the designated position in the sample read.

When the sequencing analysis (by the variant call application) produces a high count of raw fragment reads that exhibit a supporting variant (as denoted by "DS>=Threshold" in the block at 420), flow moves to 422. At 422, the incoming call is validated, namely passed as a variant or designated as a positive variant call. When the sequencing analysis produces a low count of raw fragment reads that exhibit a supporting variant, this circumstance is interpreted as an indication that an error has occurred in the potential variant call and that the variant call validation application indicates a low level of confidence that the incoming call represents a variant call. Accordingly, flow moves to 424 where the incoming variant call is invalidated, namely designated as a "negative pass".

The variant tests at 416 and 420 represent tests that exhibit a high level of confidence (relative to the confidence in other types of test) in the results there from. It is recognized that additional or alternative tests may be applied, as well as reversing the order of the tests at 416 and 420.

Returning to 406, next the hierarchy based decision tree is described in connection with the branch 412. When flow moves along branch 412, at 426, the one or more processors reviews the variant quality score assigned to the incoming variant call. When the variant quality score is less than a predetermined quality score threshold, flow moves to 428, where the incoming variant call is declared a false variant. For example, the incoming variant call is denied passage or designated as a "negative" (due to low-quality). When the variant quality score is greater than or equal to the predetermined quality score threshold, flow moves to 430. The quality score threshold utilized at 426 may be the same as or differ from the quality score threshold utilized at 416.

At 430, the one or more processors determine a weighted score (WS) associated with counts for one or more types of raw fragments. For example, the variant call application may output counts for multiple different raw fragment types, such as duplex stitched fragment, simplex stitched fragment, duplex un-stitched fragment and simplex un-stitched fragment. The counts indicate the number of reads of the raw fragments, from the corresponding type, that included a supporting variant. At 430, the processors apply weights to the counts and sum the result to obtain a weighted score that combines the different types of raw fragments. The weighted sum is compared to a weighted score (WS) threshold. When the sum of the weighted scores exceed the WS threshold, flow advances to 432. Otherwise, flow moves to 434 where the incoming variant call is not confirmed and declared invalid, denoted as a "negative pass".

At 432, the one or more processors performs a sum count of the raw fragments that validated the incoming variant call. For example, the processors may sum the counts indicate the number of reads of the raw fragments, from the corresponding type, that included a supporting variant. The sum count is compared to a sum count (SC) threshold. When the sum count falls below the SC threshold, flow moves to 436. Otherwise, flow moves to 438, where the incoming variant call is validated, namely declared a "positive pass".

At 436, the one or more processors reviews the count of the duplex stitched fragment(s) that include supporting variants (similar to the process at 420) to determine whether the duplex stitched fragment(s) authenticate/confirm the incoming variant call. The variant determination associated with the duplex stitched fragment(s) is compared to a duplex stitched (DS) threshold. When the count of DS supporting variants falls below the threshold, flow moves to 440 with the incoming variant call invalidated, namely declared a "negative pass". When the count of duplex stitched raw fragments equals or exceeds the DS threshold, at 436, flow moves to 442 where the incoming variant call is validated, namely declared to represent a "positive pass."

It is recognized that the foregoing hierarchy based decision tree represents one example of a manner in which the variant related factors may be analyzed. For example, in certain instances, the variant related factors may be rearranged to be considered in a different order within the decision tree. In connection with FIG. 4, various decisions are made based on information concerning raw fragments (e.g., duplex stitched raw fragments, weighted scores for raw fragments, variant raw fragment counts and the like). In addition, the variant quality score is used as another filter criteria. The hierarchy based decision tree uses the foregoing information to improve variant calling sensitivity and specificity, such as with ctDNA data. The hierarchy based decision tree is used to filter variants first called by a variant caller. In the embodiment of FIG. 4, weighted fragment support is used to help derive confidence in variant calls, provided that the incoming variant call matches a prior variant and the quality score exceeds a quality score threshold. The score gives different weights to different raw fragment types for each variant, including duplex/simplex and stitched/unstitched fragments. The weights may be trained from data with known results. A passing variant call has to have a sufficiently high variant Q-score calculated from comparison to normal baseline (see previous section) as well as a sufficient weighted score. However, it is recognized that the weighted fragment support may be performed at a different point in the decision tree, or omitted entirely.

In the embodiment of FIG. 4, the hierarchy based decision tree includes at least three tiers of support fragment tests that are applied before validating an incoming variant call. For example before validating an in-coming variant call at 422, raw fragment tests afford positive results at three tiers, namely at 406, 416 and 420. Before validating an incoming variant call at 438, raw fragment tests afford positive results at four tiers, namely at 406, 426 430 and 432. Before validating an incoming variant call at 442, raw fragment tests afford positive results at five tiers, namely at 406, 426, 430, 432 and 436. The number of tiers of tests that are applied to raw fragments may be varied based upon the degree of confidence afforded with any particular test.

Figure 5A:
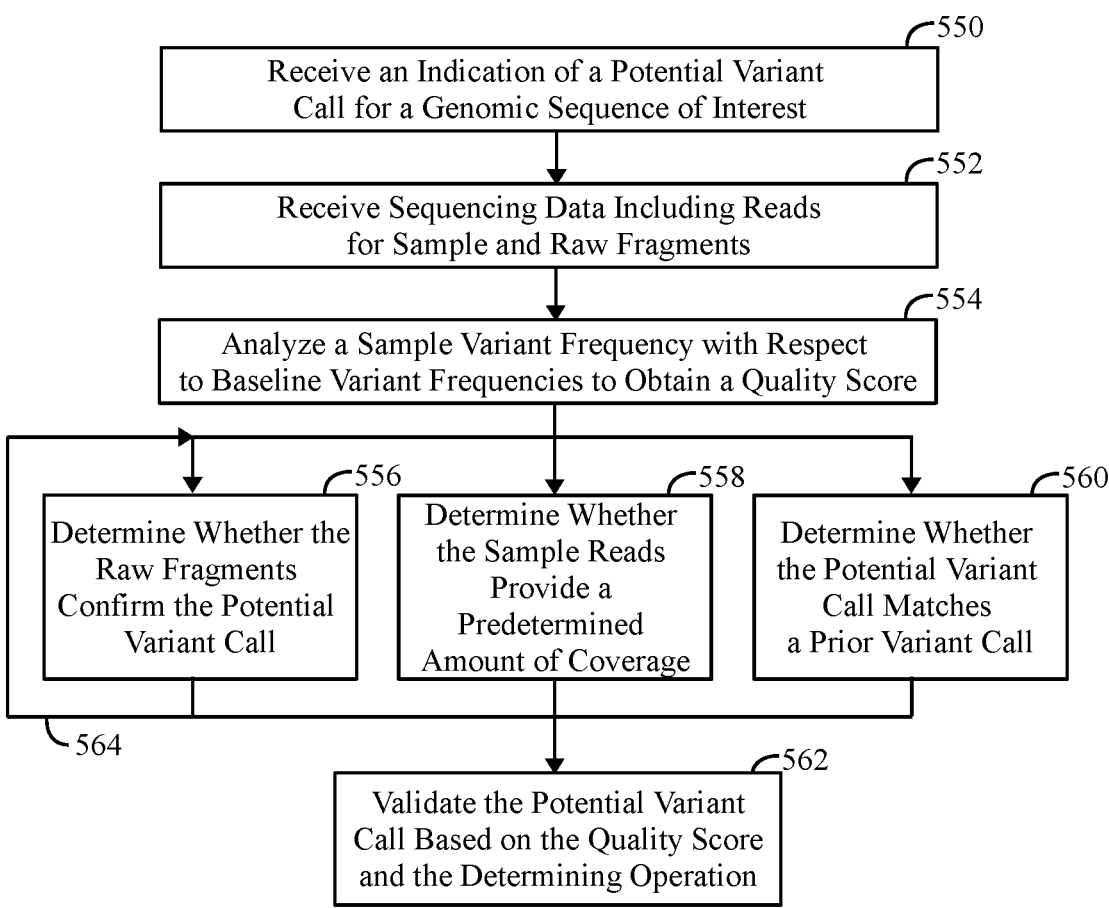
FIG. 5A illustrates a hierarchy-based decision tree to filter variant calls implemented in accordance with alternative embodiments herein.

FIG. 5A illustrates a hierarchy-based decision tree implemented in accordance with an alternative embodiment herein to filter variant calls. FIG. 5A is a generalized process, one implementation of which is presented in FIG. 4. At 550, one or more processors receive an indication of a potential variant call for a genomic sequence of interest. At 552, the one or more processors receive sequencing data including reads for sample and raw fragments of nucleotides along the genomic sequence of interest. The reads include sample reads for the sample fragment corresponding to a sequence of nucleotides at designated position along the genomic sequence of interest. 4

At 554, the one or more processors analyzes a sample variant frequency at the designated position for the genomic sequence of interest with respect to baseline variant frequencies at the designated position for a baseline genomic sequence to obtain a quality score. Next, the one or more processors perform one or more of multiple test concerning raw fragments. In the example of FIG. 5A, three determinations are illustrated at 556, 558 and 560. Optionally, the determinations at 556, 558 and 560 may be repeated (as denoted at branch 564). Additionally or alternatively, the determinations at 556, 558 and 560 may be repeated more than once in connection with different information, may be performed in any order, and may be afforded different weights in connection with validating a potential variant call. Optionally, one or more of the determinations at 556, 558 and 560 may be omitted entirely.

At 556, the one or more processors determines whether the raw fragments confirm the potential variant call. For example, the raw fragments may correspond to at least one of a duplex stitched fragment, a simplex stitched fragment, a duplex un-stitched fragment or a simplex un-stitched fragment. As one example, the determination may include identifying a count of a number duplex stitched fragments as the raw fragment that included supporting variants. The processors will determine whether the count of duplex stitched fragments that included supporting variants exceed a DS threshold, thereby confirming the potential variant call. Optionally, at 556, the processors may perform the duplex, weighted score and sum count determinations as discussed above in connection with the operations at 420, 430, 432, and 436 in FIG. 4.

At 558, the one or more processors determines whether the sample reads provide a predetermined amount of coverage for the sample fragment. The potential variant call may be declared a No-call when the sample reads fall below the predetermined amount of coverage.

At 560, the one or more processors determines whether the potential variant call matches a prior variant call exhibited across a predefined population. Correlation to a prior variant may be utilized as information to a just one or more thresholds utilized in other tests. For example, when a match is determined between the potential and prior variant calls, the determining operation performing at least one of operation 556 or operation 558 utilizing a first threshold. Additionally, when a match does not exist between the potential and prior variant calls, the determining operation performing at least one of operation 556 or operation 558 utilizing a second threshold.

At 562, the one or more processors validates the potential variant call based on the quality score and the determining operation(s). For example, a potential variant call may be validated when the quality score exceeds a quality score threshold and at least one of the determinations at 556-560 support the potential variant call. Additionally or alternatively, the determinations at 556-560 may be combined, such as through a weighted sum where the weight of each determination may be the same or different. The weighted sum of the determinations at 556-560 may be compared to a threshold and the potential variant call only validated when the weighted sum exceeds the threshold. Optionally, the importance and/or weight afforded to the determinations at 556 does 560 may be varied based upon the level of the quality score. For example, when a very high quality score is determined, to validate a potential variant call, it may be determined that only one of the determinations at 556-560 need support the potential variant call. Alternatively, when a medium level quality score is determined, to or more of the determinations at 556-560 may be needed to support a potential variant call, before validating the potential variant call. As another example, the thresholds applied to the determinations at 556-560 may be varied based on a level of the quality score.

Figure 5B:
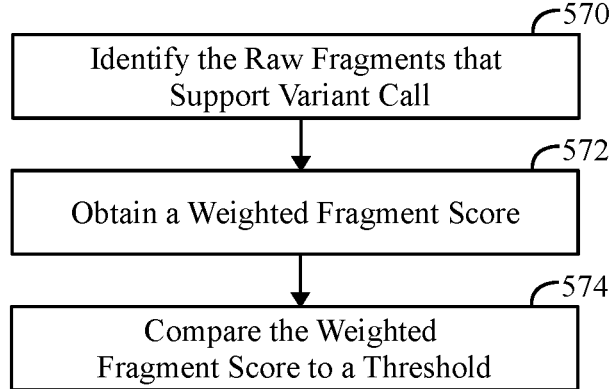
FIG. 5B illustrates a process performed in connection with utilizing a weighted score in accordance with embodiments herein.

FIG. 5B illustrates a process performed in connection with utilizing a weighted score (e.g., the operation at 430 in FIG. 4 and/or 556 in FIG. 5A) in accordance with embodiments herein. At 570, the one or more processors identifies a count of the raw fragments that include a supporting variant related to the potential variant call. At 572, the one or more processors obtains a weighted fragment score for the raw fragments that indicate the supporting variant call. For example, the count associated with the duplex stitched raw fragments may be multiplied by a first weighting factor, the count associated with the simplex stitched raw fragments may be multiplied by a second weighting factor, the count associated with the duplex un-stitched fragments may be multiplied by a third weighting factor and the count associated with the simplex unstitched fragments may be multiplied by a fourth weighting factor. The first through fourth weighting factors may then be summed or combined in some other manner to obtain a weighted fragment score. Additionally or alternatively, the weighting fragment score may be modified based upon the number of raw fragments that did not include supporting variants. For example, when a large number of supporting fragments correspond to a reference sequence, the count of the raw fragments (matching the reference sequence) may be utilized as a factor to decrease the weighted fragment score. At 574, the one or more processors compares the weighted fragment score to a raw fragment threshold to determine whether to confirm the potential variant call.

Computer-Implemented Aspects

As understood by those of ordinary skill in the art, the methods and information described herein may be implemented, in all or in part, as computer executable instructions on known computer readable media. For example, the methods described herein may be implemented in hardware. Alternatively, the method may be implemented in software stored in, for example, one or more memories or other computer readable medium and implemented on one or more processors. As is known, the processors may be associated with one or more controllers, calculation units and/or other units of a computer system, or implanted in firmware as desired. If implemented in software, the routines may be stored in any computer readable memory such as in RAM, ROM, flash memory, a magnetic disk, a laser disk, or other storage medium, as is also known. Likewise, this software may be delivered to a computing device via any known delivery method including, for example, over a communication channel such as a telephone line, the Internet, a wireless connection, etc., or via a transportable medium, such as a computer readable disk, flash drive, etc. More generally, and as understood by those of ordinary skill in the art, the various steps described above may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any known computer readable medium such as on a magnetic disk, an optical disk, or other storage medium, in a RAM or ROM or flash memory of a computer, processor, hard disk drive, optical disk drive, tape drive, etc. Likewise, the software may be delivered to a user or a computing system via any known delivery method including, for example, on a computer readable disk or other transportable computer storage mechanism.

Figure 6:
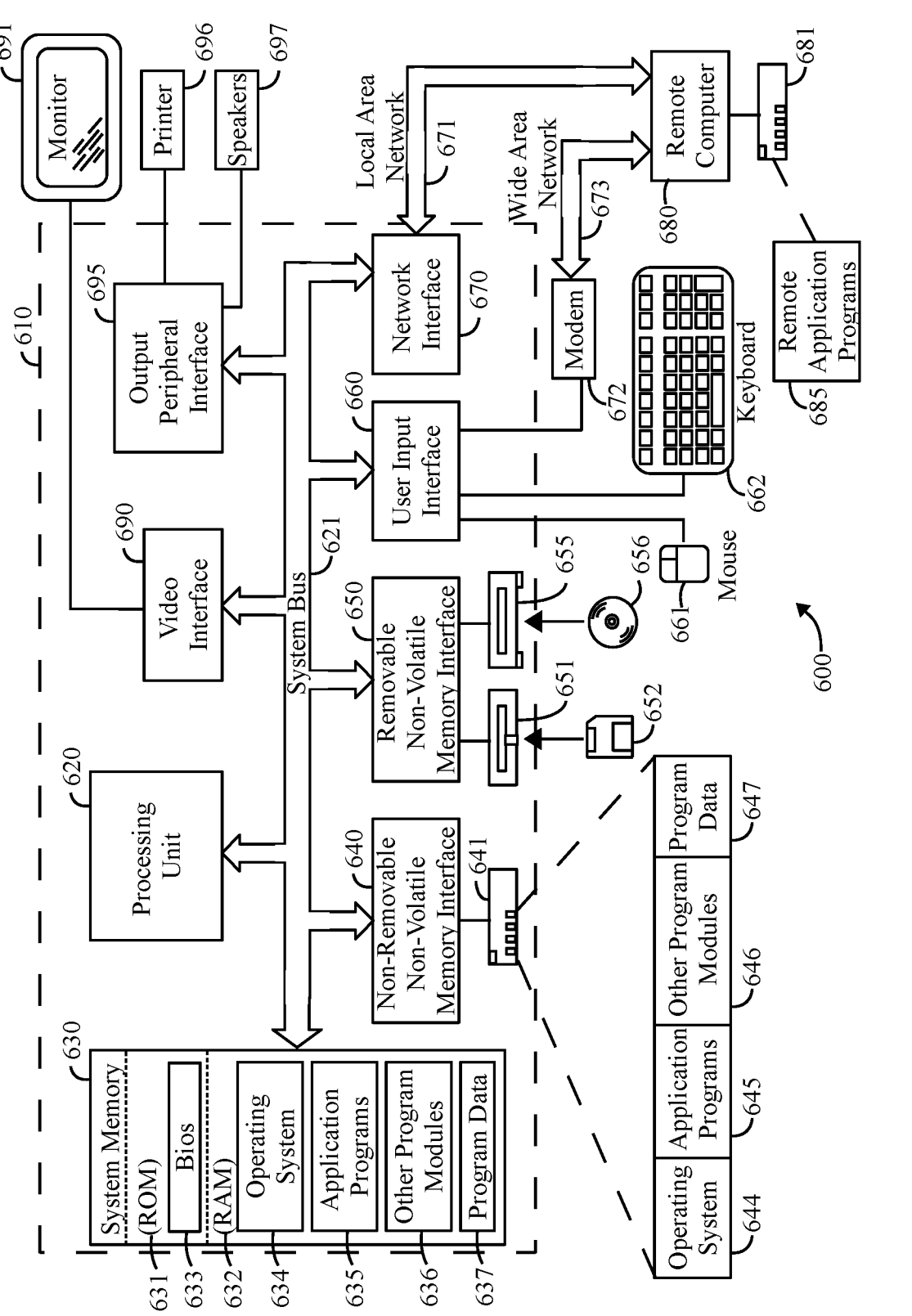
FIG. 6 illustrates a block diagram of a computing system environ formed in accordance with embodiments herein.

FIG. 6 illustrates a block diagram of a computing system environment 600 formed in accordance with an embodiment herein. The computing system environment 600 is only one example of a suitable computing environment and is not intended to suggest any limitation as to the scope of use or functionality herein. Neither should the computing environment 600 be interpreted as having any dependency or requirement relating to any one or combination of components illustrated in the exemplary operating environment 600. The methods and systems are operational with numerous other general purpose or special purpose computing system environments or configurations. Examples of computing systems, environments, and/or configurations that may be suitable for use with the methods or system of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The operations of the methods and systems may be described in the general context of computer-executable instructions, such as program modules, being executed by a computer. Generally, program modules include routines, programs, objects, components, data structures, etc. that perform particular tasks or implement particular abstract data types. The methods and apparatus may also be practiced in distributed computing environments where tasks are performed by remote processing devices that are linked through a communications network. In both integrated and distributed computing environments, program modules may be located in both local and remote computer storage media including memory storage devices.

With reference to FIG. 6, components of computer 610 may include, but are not limited to, a processing unit 620, a system memory 630, and a system bus 621 that couples various system components including the system memory to the processing unit 620. The system bus 621 may be any of several types of bus structures including a memory bus or memory controller, a peripheral bus, and a local bus using any of a variety of bus architectures. By way of example, and not limitation, such architectures include Industry Standard Architecture (USA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 610 typically includes a variety of computer readable media. Computer readable media can be any available media that can be accessed by computer 610 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 610. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 630 includes computer storage media in the form of volatile and/or nonvolatile memory such as read only memory (ROM) 631 and random access memory (RAM) 632. A basic input/output system 633 (BIOS), containing the basic routines that help to transfer information between elements within computer 610, such as during start-up, is typically stored in ROM 631. RAM 632 typically contains data and/or program modules that are immediately accessible to and/or presently being operated on by processing unit 620. By way of example, and not limitation, FIG. 6 illustrates operating system 634, application programs 635, other program modules 636, and program data 637.

The computer 610 may also include other removable/non-removable, volatile/nonvolatile computer storage media. By way of example only, FIG. 6 illustrates a hard disk drive 640 that reads from or writes to non-removable, nonvolatile magnetic media, a magnetic disk drive 651 that reads from or writes to a removable, nonvolatile magnetic disk 652, and an optical disk drive 655 that reads from or writes to a removable, nonvolatile optical disk 656 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 641 is typically connected to the system bus 621 through a non-removable memory interface such as interface 640, and magnetic disk drive 651 and optical disk drive 655 are typically connected to the system bus 621 by a removable memory interface, such as interface 650.

The drives and the associated computer storage media discussed above and illustrated in FIG. 6, provide storage of computer readable instructions, data structures, program modules and other data for the computer 610. In FIG. 6, for example, hard disk drive 641 is illustrated as storing operating system 644, application programs 645, other program modules 646, and program data 647. Note that these components can either be the same as or different from operating system 634, application programs 635, other program modules 636, and program data 637. Operating system 644, application programs 645, other program modules 646, and program data 647 are given different numbers here to illustrate that, at a minimum, they are different copies. A user may enter commands and information into the computer through input devices such as a keyboard 662 and pointing device 661, commonly referred to as a mouse, trackball or touch pad. Other input devices (not shown) may include a microphone, joystick, game pad, satellite dish, scanner, or the like. These and other input devices are often connected to the processing unit 620 through a user input interface 660 that is coupled to the system bus, but may be connected by other interface and bus structures, such as a parallel port, game port or a universal serial bus (USB). A monitor 691 or other type of display device is also connected to the system bus 621 via an interface, such as a video interface 690. In addition to the monitor, computers may also include other peripheral output devices such as speakers 697 and printer 696, which may be connected through an output peripheral interface 695.

The computer 610 may operate in a networked environment using logical connections to one or more remote computers, such as a remote computer 680. The remote computer 680 may be a personal computer, a server, a router, a network PC, a peer device or other common network node, and typically includes many or all of the elements described above relative to the computer 610, although only a memory storage device 681 has been illustrated in FIG. 6. The logical connections depicted in FIG. 6 include a local area network (LAN) 671 and a wide area network (WAN) 673, but may also include other networks. Such networking environments are commonplace in offices, enterprise-wide computer networks, intranets and the Internet.

When used in a LAN networking environment, the computer 610 is connected to the LAN 671 through a network interface or adapter 670. When used in a WAN networking environment, the computer 610 typically includes a modem 672 or other means for establishing communications over the WAN 673, such as the Internet. The modem 672, which may be internal or external, may be connected to the system bus 621 via the user input interface 660, or other appropriate mechanism. In a networked environment, program modules depicted relative to the computer 610, or portions thereof, may be stored in the remote memory storage device. By way of example, and not limitation, FIG. 6 illustrates remote application programs 685 as residing on memory device 681. It will be appreciated that the network connections shown are exemplary and other means of establishing a communications link between the computers may be used.

While the risk evaluation system and method, and other elements, have been described as preferably being implemented in software, they may be implemented in hardware, firmware, etc., and may be implemented by any other processor. Thus, the elements described herein may be implemented in a standard multi-purpose CPU or on specifically designed hardware or firmware such as an application-specific integrated circuit (ASIC) or other hard-wired device as desired, including, but not limited to, the computer 610 of FIG. 6. When implemented in software, the software routine may be stored in any computer readable memory such as on a magnetic disk, a laser disk, or other storage medium, in a RAM or ROM of a computer or processor, in any database, etc. Likewise, this software may be delivered to a user or a diagnostic system via any known or desired delivery method including, for example, on a computer readable disk or other transportable computer storage mechanism or over a communication channel such as a telephone line, the internet, wireless communication, etc. (which are viewed as being the same as or interchangeable with providing such software via a transportable storage medium). Thus, many modifications and variations may be made in the techniques and structures described and illustrated herein without departing from the spirit and scope of the present invention. Thus, it should be understood that the methods and apparatus described herein are illustrative only and are not limiting upon the scope of the invention.

Figure 7:
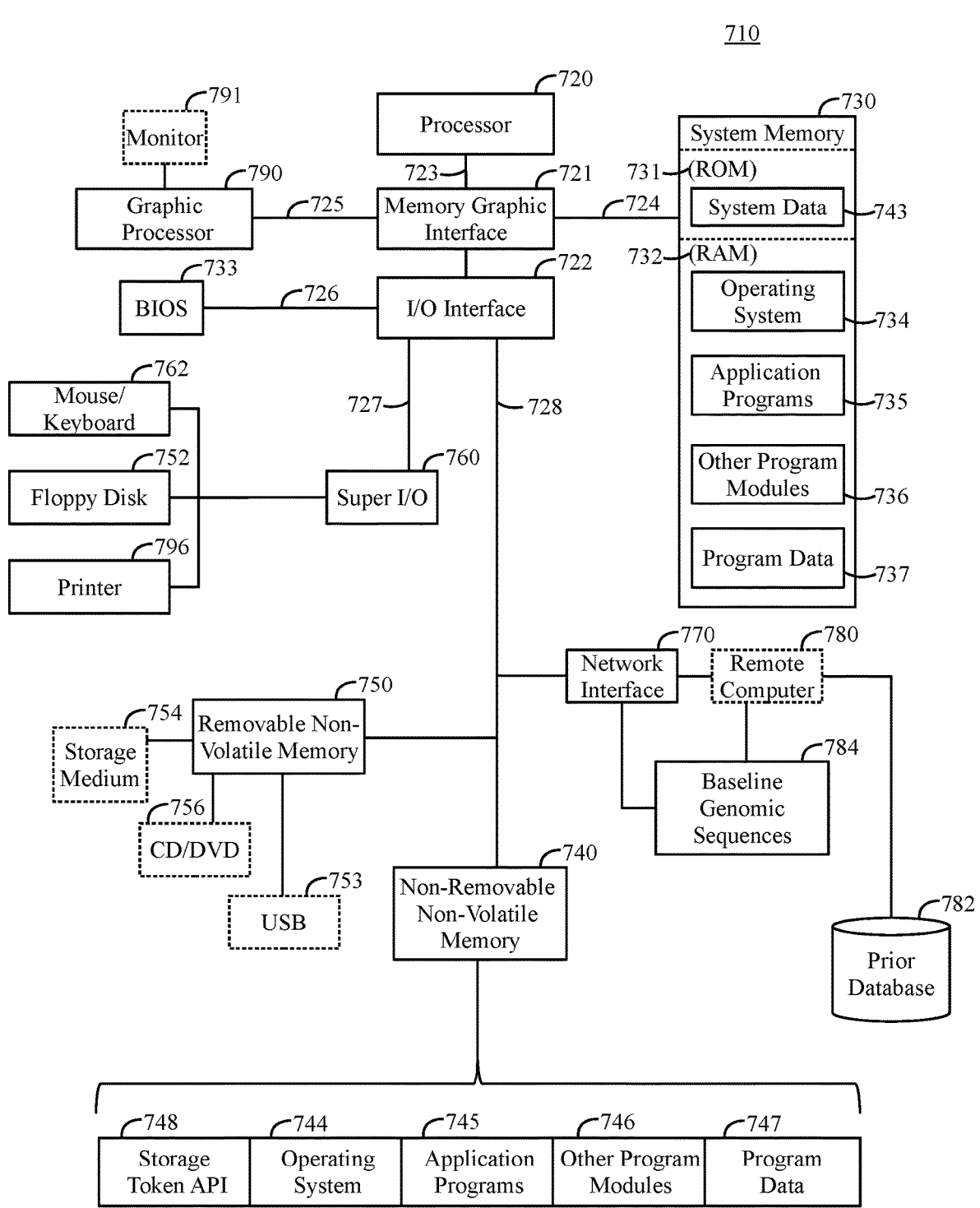
FIG. 7 illustrates a block diagram of an alternative system formed in accordance with embodiments herein.

FIG. 7 illustrates a block diagram of an alternative system formed in accordance with an embodiment herein. Components shown in dashed outline are not technically part of the computer 710, but are used to illustrate the exemplary embodiment of FIG. 7. Components of computer 710 may include, but are not limited to, a processor 720, a system memory 730, a memory/graphics interface 721, also known as a Northbridge chip, and an I/O interface 722, also known as a Southbridge chip. The system memory 730 and a graphics processor 790 may be coupled to the memory/graphics interface 721. A monitor 791 or other graphic output device may be coupled to the graphics processor 790.

A series of system busses may couple various system components including a high speed system bus 723 between the processor 720, the memory/graphics interface 721 and the I/O interface 722, a front-side bus 724 between the memory/graphics interface 721 and the system memory 730, and an advanced graphics processing (AGP) bus 725 between the memory/graphics interface 721 and the graphics processor 790. The system bus 723 may be any of several types of bus structures including, by way of example, and not limitation, such architectures include Industry Standard Architecture (USA) bus, Micro Channel Architecture (MCA) bus and Enhanced ISA (EISA) bus. As system architectures evolve, other bus architectures and chip sets may be used but often generally follow this pattern. For example, companies such as Intel and AMD support the Intel Hub Architecture (IHA) and the Hypertransport™ architecture, respectively.

The computer 710 typically includes a variety of computer-readable media. Computer-readable media can be any available media that can be accessed by computer 710 and includes both volatile and nonvolatile media, removable and non-removable media. By way of example, and not limitation, computer readable media may comprise computer storage media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other physical medium which can be used to store the desired information and which can accessed by computer 710.

The system memory 730 includes computer storage media in the form of volatile and/or nonvolatile memory such as read only memory (ROM) 731 and random access memory (RAM) 732. The system ROM 731 may contain permanent system data 743, such as identifying and manufacturing information. In some embodiments, a basic input/output system (BIOS) may also be stored in system ROM 731. RAM 732 typically contains data and/or program modules that are immediately accessible to and/or presently being operated on by processor 720. By way of example, and not limitation, FIG. 5 illustrates operating system 734, application programs 735, other program modules 736, and program data 737.

The I/O interface 722 may couple the system bus 723 with a number of other busses 726, 727 and 728 that couple a variety of internal and external devices to the computer 710. A serial peripheral interface (SPI) bus 726 may connect to a basic input/output system (BIOS) memory 733 containing the basic routines that help to transfer information between elements within computer 710, such as during start-up.

A super input/output chip 760 may be used to connect to a number of 'legacy' peripherals, such as floppy disk 752, keyboard/mouse 762, and printer 796, as examples. The super I/O chip 760 may be connected to the I/O interface 722 with a bus 727, such as a low pin count (LPC) bus, in some embodiments. Various embodiments of the super I/O chip 760 are widely available in the commercial marketplace. In one embodiment, bus 728 may be a Peripheral Component Interconnect (PCI) bus, or a variation thereof, may be used to connect higher speed peripherals to the I/O interface 722. A PCI bus may also be known as a Mezzanine bus. Variations of the PCI bus include the Peripheral Component Interconnect-Express (PCI-E) and the Peripheral Component Interconnect-Extended (PCI-X) busses, the former having a serial interface and the latter being a backward compatible parallel interface. In other embodiments, bus 728 may be an advanced technology attachment (ATA) bus, in the form of a serial ATA bus (SATA) or parallel ATA (PATA).

The computer 710 may also include other removable/non-removable, volatile/nonvolatile computer storage media. By way of example only, FIG. 7 illustrates a hard disk drive 740 that reads from or writes to non-removable, nonvolatile magnetic media. The hard disk drive 740 may be a conventional hard disk drive. Removable media, such as a universal serial bus (USB) memory 753, firewire (IEEE 7394), or CD/DVD drive 756 may be connected to the PCI bus 728 directly or through an interface 750. A storage media 754 may coupled through interface 750. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like.

The drives and their associated computer storage media discussed above and illustrated in FIG. 7, provide storage of computer readable instructions, data structures, program modules and other data for the computer 710. In FIG. 7, for example, hard disk drive 740 is illustrated as storing storage token API 748, operating system 744, application programs 745, other program modules 746, and program data 747. Note that these components can either be the same as or different from operating system 734, application programs 735, other program modules 736, and program data 737. Storage token API 748, operating system 744, application programs 745, other program modules 746, and program data 747 are given different numbers here to illustrate that, at a minimum, they are different copies. A user may enter commands and information into the computer through input devices such as a mouse/keyboard 762 or other input device combination. Other input devices (not shown) may include a microphone, joystick, game pad, satellite dish, scanner, or the like. These and other input devices are often connected to the processor 720 through one of the I/O interface busses, such as the SPI 726, the LPC 727, or the PCI 728, but other busses may be used. In some embodiments, other devices may be coupled to parallel ports, infrared interfaces, game ports, and the like (not depicted), via the super I/O chip 760. The computer 710 may operate in a networked environment using logical connections to one or more remote computers, such as a remote computer 780 via a network interface controller (NIC) 770. The remote computer 780 may be a personal computer, a server, a router, a network PC, a peer device or other common network node, and typically includes many or all of the elements described above relative to the computer 710. The logical connection between the NIC 770 and the remote computer 780 depicted in FIG. 7 may include a local area network (LAN), a wide area network (WAN), or both, but may also include other networks. Such networking environments are commonplace in offices, enterprise-wide computer networks, intranets, and the Internet. The remote computer 780 may also represent a web server supporting interactive sessions with the computer 710, or in the specific case of location-based applications may be a location server or an application server. The remote computer 780 may represent a server that manages a baseline genomic sequence database 784, a prior database 782 and the like. For example, as explained herein, the baseline genomic sequence database 784 is periodically updated with new baseline information. The database 784 is accessed in connection with validating potential variant calls for samples (e.g., to obtain baseline variant frequencies at designated positions). As another example, the prior database 782 may also be accessed in connection with validating potential variant calls for samples (e.g., to determine whether a potential variant call corresponds to a prior variant).

In some embodiments, the network interface may use a modem (not depicted) when a broadband connection is not available or is not used. It will be appreciated that the network connection shown is exemplary and other means of establishing a communications link between the computers may be used. Exemplary processors (processing units) include all variety of microprocessors and other processing units used in computing devices. Exemplary computer-readable media are described above. When two or more components of the system involve a processor or a computer-readable medium, the system generally can be created where a single processor and/or computer readable medium is dedicated to a single component of the system; or where two or more functions share a single processor and/or share a single computer readable medium, such that the system contains as few as one processor and/or one computer readable medium. In some variations, it is advantageous to use multiple processors or media, for example, where it is convenient to have components of the system at different locations. For instance, some components of a system may be located at a testing laboratory dedicated to laboratory or data analysis, whereas other components, including components (optional) for supplying input information or obtaining an output communication, may be located at a medical treatment or counseling facility (e.g., doctor's office, health clinic, HMO, pharmacist, geneticist, hospital) and/or at the home or business of the human subject (patient) for whom the testing service is performed.

The remote computer 780 may represent a server or other network resource that is communicatively coupled to a prior database 782 and that contains population information correlating the presence or absence of variants/alleles in a population of humans. For example, the one or more variants/alleles include mutant alleles that cause, or are indicative of, select defects. In a simple variation, the prior database 782 contains data relating to the frequency that select alleles have been observed in a population of humans, for example with bladder cancer, and a population of humans, for example free of bladder cancer. Additionally or alternatively, the prior database may include similar data with respect to two or more alleles, thereby providing a useful reference if the human subject has any of the two or more alleles. Additionally or alternatively, the prior database may include additional quantitative personal, medical, or genetic information about the individuals in the database diagnosed with or without a condition. Such information includes, but is not limited to, information about parameters such as age, sex, ethnicity, race, medical history, weight, diabetes status, blood pressure, family history of bladder cancer, smoking history, and alcohol use in humans and impact of the at least one parameter concerning a prior. The prior also can include information about other genetic risk factors for alleles.

A baseline genomic sequence database or library 784 may be provided to store baseline genomic sequences that are utilized, in accordance with embodiments herein, to identify baseline variant frequencies and other information.

What is claimed is:

1. A computer implemented method for validating variant calls to reduce false positive variant calling from systemic errors, the method comprising:

receiving a sample containing polynucleotides;

preparing the sample containing polynucleotides for sequencing;

sequencing the sample to generate a plurality of sample reads from the polynucleotides;

wherein said sequencing comprises analyzing multiple different samples in the same sequencing run, thereby reducing sequencing depth of coverage per sample; and under control of one or more processors executing program instructions for:

receiving sequencing data in a binary file format, the sequencing data including at least 10,000 sample reads from the plurality of sample reads, each sample read having a corresponding sequence of nucleotides along a genomic sequence of interest;

receiving an indication of a potential variant call at a designated position within each corresponding sequence of nucleotides along the genomic sequence of interest;

determining baseline variant frequencies at the designated position within one or more baseline genomic sequences, the baseline variant frequencies representing relative frequencies of a variant at a particular position along one or more baseline genomic sequences in a population, the population corresponding to the number of reads and/or samples obtained from the one or more baseline genomic sequences from a population of normal individuals;

determining a sample variant frequency at the designated position for the genomic sequence of interest, the sample variant frequency representing a relative frequency of a variant at the particular position along the genomic sequence of interest in a population, the population corresponding to the number of sample reads obtained for the genomic sequence of interest from an individual;

analyzing the baseline and sample variant frequencies at the designated position to generate a quality score, the analyzing comprising indexing the sample variant frequency with respect to a distribution of the baseline variant frequencies; and validating the potential variant call for the genomic sequence of interest based on the quality score, the validating comprising comparing the quality score to a threshold using a hierarchical decision tree for multi-level validation, wherein a quality score that exceeds the threshold indicates a valid variant call and a quality score that is less than the threshold indicates a false variant, thereby reducing false positive variant calling from systematic error at a lower depth of coverage;

wherein the determining of the baseline variant frequencies comprises:

a) receiving the sequencing data from reference reads for a set of positions within a current base pair window, wherein a length of the current base pair window comprises a plurality of base pairs;

b) identifying a candidate variant frequency for one or more positions in the set of positions within the current base pair window;

c) selecting one of the one or more candidate variant frequencies as a single baseline variant frequency for the designated position within the reference reads; and d) shifting the base pair window along one or more of the baseline genomic sequences and repeating the operations at a), b), and c) to determine baseline variant frequencies at a next designated position.

2. The method of claim 1, wherein the analyzing further comprises generating a relation between the sample variant frequency and the distribution of the baseline variant frequencies, the quality score based on the relation.

3. The method of claim 2, wherein the relation is based on a non-parametric Wilcoxon rank sum test.

4. The method of claim 1, wherein the baseline variant frequencies indicate a degree of background noise at corresponding positions along the baseline genomic sequence.

5. The method of claim 1, wherein the validating further comprises declaring the potential variant call to be a valid variant call when the quality score exceeds the threshold.

6. The method of claim 1, wherein the baseline variant frequencies are derived from multiple baseline genomic sequences that are associated with more than one type of allele.

7. The method of claim 1, further comprising receiving sequencing data that includes a plurality of reference reads of a sequence of nucleotides along the baseline genomic sequence, and determining the baseline variant frequencies for the reference reads at each designated position.

8. The method of claim 1, wherein the preparing comprises amplifying predetermined genetic loci within the polynucleotides that are known to include short tandem repeats (STRs) or single nucleotide polymorphisms (SNPs).

9. The method of claim 1, wherein the binary file format is a Binary Alignment Map (BAM).

10. The method of claim 1, wherein the sample comprises sputum/oral fluid, amniotic fluid, blood, a blood fraction, fine needle biopsy samples, urine, peritoneal fluid, pleural fluid, tissue explant, organ culture and any other tissue or cell preparation, or fraction or derivative thereof or isolated therefrom.

11. The method of claim 1, wherein the sequencing comprises a sequencing by synthesis method (SBS).

12. The method of claim 1, wherein the threshold represents a Q-score cut-off to filter out potential false variants.

* * * * *